(12) United States Patent
Lukac et al.

(10) Patent No.: US 11,648,417 B2
(45) Date of Patent: May 16, 2023

(54) APPARATUS AND METHOD FOR TISSUE REGENERATION

(71) Applicant: Fotona d.o.o., Ljubljana (SI)

(72) Inventors: Matjaz Lukac, Ljubljana (SI); Franci Bajd, Ljubljana (SI); Marko Kazic, Ljubljana (SI); Zdenko Vizintin, Ljubljana (SI); Tadej Perhavec, Ljubljana (SI)

(73) Assignee: Fotona d.o.o., Ljubljana (SI)

( * ) Notice: Subject to any disclaimer, the term of this patent is extended or adjusted under 35 U.S.C. 154(b) by 40 days.

(21) Appl. No.: 16/411,608

(22) Filed: May 14, 2019

(65) Prior Publication Data

US 2019/0351253 A1    Nov. 21, 2019

(30) Foreign Application Priority Data

May 15, 2018   (EP) .................................... 18172363

(51) Int. Cl.
  *A61N 5/06*      (2006.01)
  *A61B 1/307*    (2006.01)
  *A61N 5/067*    (2006.01)

(52) U.S. Cl.
  CPC ............ *A61N 5/0625* (2013.01); *A61B 1/307* (2013.01); *A61N 5/067* (2021.08);
  (Continued)

(58) Field of Classification Search
  CPC .......... A61N 5/0625; A61N 2005/0642; A61N 2005/0643; A61N 2005/0644; A61N 2005/067
  See application file for complete search history.

(56) References Cited

U.S. PATENT DOCUMENTS 6,077,294 A   6/2000  Cho et al.
10,588,694 B1 * 3/2020  Neev .................... A61B 18/203
(Continued)

OTHER PUBLICATIONS

Nemes et al, "Dependence of Skin Ablation Depths on Er:YAG Laser Fluence", 2014, Journal of the Laser and Health Academy (Year: 2014).*

(Continued)

*Primary Examiner* — Lynsey C Eiseman
*Assistant Examiner* — Jessica L Mullins
(74) *Attorney, Agent, or Firm* — Renner, Otto, Boisselle & Sklar, LLP

(57) ABSTRACT

An apparatus for tissue regeneration is provided. The apparatus comprises means for generating at least one laser pulse comprising a wavelength; and means for directing the at least one laser pulse onto a tissue surface of a human or animal body, wherein the means for generating comprises control means to ensure that a sum of the pulse energies of the at least one laser pulse is selected so that the corresponding fluence on the tissue surface heats the tissue surface up to a maximal temperature $T_{max}$ between 70° C. and a tissue boiling temperature $T_b$. Further, the means for generating of the apparatus are adapted so that a delivery time $t_{ed}$ of the at least one laser pulse (during which the second half of the pulse energy is delivered) is sufficiently short so that, given the wavelength and thus a corresponding penetration depth $\delta$ of the at least one laser pulse, a thermal exposure time $t_{exp}$ of the tissue surface is shorter than 900 microseconds. Here, the thermal exposure time $t_{exp}$ of the tissue surface is defined as a time interval in which the temperature of the tissue surface is above $T_o+(T_{max}-T_o)/2$, wherein $T_o$ defines the initial temperature of the tissue surface, before the laser pulse arrives.

12 Claims, 8 Drawing Sheets

(52) U.S. Cl.
CPC ............... *A61N 2005/0643* (2013.01); *A61N 2005/0644* (2013.01); *A61N 2005/0659* (2013.01)

(56) References Cited

U.S. PATENT DOCUMENTS

| | | | |
|---|---|---|---|
| 2003/0028180 A1* | 2/2003 | Franco | A61B 18/20 606/14 |
| 2008/0214988 A1 | 9/2008 | Altshuler et al. | |
| 2008/0234669 A1* | 9/2008 | Kauvar | B23K 26/0096 606/9 |
| 2012/0179229 A1* | 7/2012 | Tettamanti | A61N 5/0603 607/89 |
| 2015/0126913 A1 | 5/2015 | Jurna et al. | |

OTHER PUBLICATIONS

Matjaz Lukac et al, "Dual Tissue Regeneration: Non-Ablative Resurfacing of Soft Tissues with FotonaSmooth Mode Er:YAG Laser", Journal of Laser and Health Academy, vol. 2018, No. 1 (Year: 2018).*

Extended European Search Report for corresponding European U.S. Appl. No. 18/172,363 dated Oct. 25, 2019.

European Communication pursuant to Article 94(3) EPC for corresponding European Patent Application No. 18 172 363.6 dated Jul. 23, 2020.

* cited by examiner

APPARATUS AND METHOD FOR TISSUE REGENERATION

This application claims priority to European Patent Application No. 18172363.6 filed on May 15, 2018, which is hereby incorporated herein by reference.

FIELD OF THE INVENTION

The present invention relates to an apparatus and a method for tissue regeneration. The goal of the treatment is the rejuvenation of the tissue by stimulating its regenerative potential.

TECHNICAL BACKGROUND

Nowadays, lasers are used for treating a wide variety of disorders and cosmetic conditions, in particular the rejuvenation of skin, mucosa or other tissue. Various treatments have been classified as rejuvenation treatments, such as, for example, skin resurfacing and skin tightening, as well as vascular, pigment and acne treatments. In what follows we use the expression tissue rejuvenation more narrowly to describe a treatment where the tissue (e.g., one or more layers of the tissue) is thermally injured in a non-ablative or minimally ablative and/or reversible manner. In the subsequent wound healing process, the tissue experiences a certain degree of regeneration. Such tissue regeneration is performed not only for cosmetic reasons, i.e. to make the patient's skin appear younger, but has also been found effective in treating various disorders such as incontinence, atrophy, prolapse, vaginal laxity or anal conditions.

In what follows, the terms "tissue" or "human tissue" will be used to represent both human and animal tissue. Similarly, the terms "rejuvenation" and "regeneration" will be used interchangeably.

Figure 1:
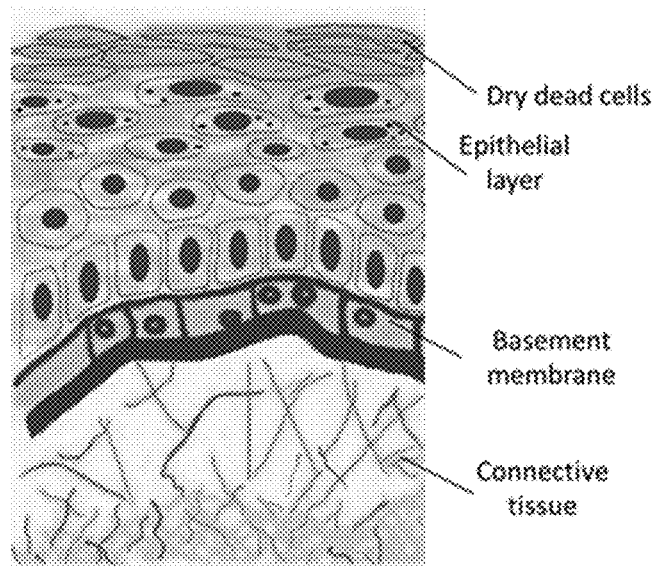

The human body consists of several types of the tissue, among them the epithelial tissue and the connective tissue (cf. FIG. 1). Epithelial tissue covers most of internal and external surfaces of the body and its organs. Epithelial tissue forms boundaries between different environments, and nearly all substances must pass through an epithelium. In its role as an interface tissue, epithelium accomplishes many functions, including protection of the underlying tissues from physical trauma and the detection of sensation. The principal cell type that is found in epithelia are keratinocytes that generate biomolecules necessary for the stability and resistance of the epithelial layer to mechanical stress. In skin, the very thin top layer of the epithelium consists of dry dead cells (cf. FIG. 1).

The type of epithelial tissue that lines various cavities in the body, such as the mouth or vagina, and covers the surface of internal organs is the mucous membrane or mucosa. Another type of the epithelial tissue is the epidermis which covers the skin surface.

The epithelial tissue and the underlying connective tissue are separated by the basement membrane, a thin, fibrous, extracellular matrix of tissue. The connective tissue lies below the epithelial tissue and helps to hold the body together. The cells of connective tissue include fibroblasts, adipocytes, macrophages, mast cells and leucocytes. Fibroblasts are the most common cells of connective tissue. A fibroblast is a type of cell that synthesizes the extracellular matrix and collagen and plays a critical role in wound healing.

In the case of the human skin, the connective tissues are part of the dermis which is a layer of skin between the epidermis and subcutaneous tissues. The oral and vaginal connective tissue is termed lamina propria. Similarly, the lumen of the urethra is surrounded by epithelium which, in turn, is surrounded by collagen-rich connective tissue and a muscle layer.

Since it is the connective tissue which is responsible for holding the skin, vagina and other organs together, previous rejuvenation techniques have typically focused on regenerating the connective tissues such as the dermis or the lamina propria. Such a regeneration mechanism is based on injuring the connective tissue, in order to induce a reactive inflammatory response which results in an increase of the biosynthetic capacity of fibroblasts and other cells. This leads to the reconstruction of an optimal physiologic environment, the enhancement of cell activity, hydration, and the synthesis of collagen, elastin and HA (hyaluronic acid). Typically, the inflammation is achieved by delivering heat to the connective tissue resulting in an increased temperature ($\Delta T$) of the target tissue.

As will be explained below, assuming a single biochemical process the thermal damage to the tissue has as an approximately exponential dependence on the exposure temperature T and a linear dependence on the exposure time ($t_{exp}$) and can be approximately described by the Arrhenius integral relation. This relation predicts that, for a one order of magnitude decrease of the exposure time, the treatment temperature can be increased by approximately five degrees. Therefore, shorter exposure times are safer and also allow more intense treatments because of the higher acceptable exposure temperature.

When using a laser to create a laser pulse, the duration and the shape of the resulting thermal exposure pulse within the tissue typically does not follow the duration and the shape of the delivered laser pulse. This is, because the volume of the heated tissue is typically relatively large, and the major mechanism by which this large volume cools down is the relatively slow diffusion of the deposited heat into the surrounding unheated tissues. It is therefore the thermal diffusion rather than the temporal pulse width of the delivered laser pulse which typically sets the lower limit for the achievable exposure time. Typical cooling times of the connective tissues are in the order of seconds or longer. This limits the treatment temperatures for the regeneration of the connective tissue to about 45 to 70° C.

It should be noted, however, that, in spite of the fact that the allowed regeneration temperatures are relatively low, it is a considerable challenge to heat up the deeper lying connective tissue to these temperatures. This is, because the delivered laser pulse must first traverse the epithelial layer located above the basement membrane, before the laser pulse can reach the fibroblasts. This means that the delivered pulse energy may be predominantly absorbed by the superficial layers. Accordingly, the maximally allowed temperatures for the epithelial layer limit the temperatures which can be generated within the connective tissues. Thus, the physician is often faced with a trade-off between using enough energy for an effective therapy and staying within the damage thresholds for the superficial tissue. To a certain degree, this limitation may be overcome by applying external cooling of the superficial layer prior or during the treatment. However, in many applications, such as when treating narrow body cavities (for example vagina, urethra or anus), such a cooling may not be clinically desirable or technically feasible.

It follows from the above that the rejuvenation devices and methods are typically designed for thermally bypassing the superficial layer to the largest extent possible, in order to be able to directly thermally activate the deeper lying fibroblasts in a safe manner. This approach is based on the conventional wisdom that an injury of the connective tissue which leads to an inflammatory response is essential for promoting collagen production. Further, it is believed that an inflammation of the connective tissue is needed to attract cells to the site of injury such as neutrophils and macrophages which, in turn, release growth factors and cytokines responsible for repair.

However, it should be noted that not only the fibroblasts but also the superficially located keratinocytes are involved in the wound healing process. In particular, it is well-known that keratinocytes recruit, stimulate and coordinate the actions of multiple cell types involved in healing. Besides, keratinocytes and fibroblasts communicate with each other via double paracrine signalling loops (known as cross talk or dynamic reciprocity) which coordinate their actions to restore normal tissue homeostasis after the wounding. In response to paracrine signalling from keratinocytes and inflammatory cells, fibroblasts synthesize collagen and promote cross-linking to form an extracellular matrix.

Accordingly, an apparatus and a method are desired which focus on an intense and safe thermal activation of the superficially located epithelia instead of bypassing the superficial layer for reversibly injuring the deeper located connective tissue.

Further, there has been a prejudice in the prior art that regeneration methods should not heat up the treated tissue to more than 70° C., since otherwise significant tissue damage would occur due to protein denaturalization.

Terminology

Before we turn to the present invention, we first define some quantities which are important for explaining the present invention. The basic setting of the present invention is that a laser pulse having a finite width impinges on the surface of a tissue. On the tissue surface, the laser beam gives rise to a spot S, wherein the spot S can be defined as the region of the tissue surface within which 90% of the total energy of the laser pulse is delivered to the tissue (i.e., the spot S corresponds to the smallest region on the tissue surface so that, during the delivery of the laser pulse, 90% of the total energy of the laser pulse is delivered to this region).

Figure 2:
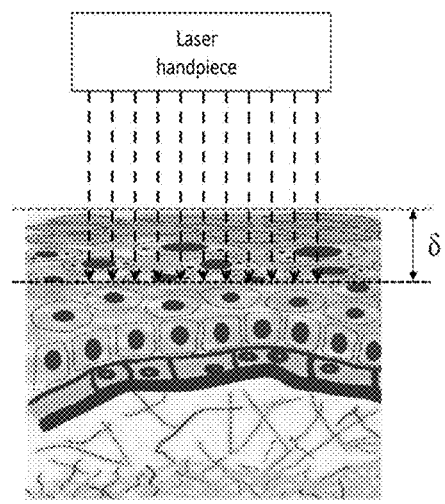

Referring to FIG. 2, the energy of the laser pulse partially transmits through the tissue surface and passes the tissue down to a penetration depth δ, wherein the penetration depth represents the inverse of the absorption coefficient within the tissue at the wavelength of the laser beam.

As the energy of the laser pulse is mainly absorbed within the superficial layer of the tissue which has the depth δ, this superficial layer of the tissue is rapidly heated up from the initial tissue temperature $T_o$ to a maximum temperature $T_{max}$.

Further, it is noted that the tissue temperature increase $\Delta T(t)$ during a laser intensity pulse I(t) (in W) is not proportional to I(t) but to the cumulative laser energy E(t) (in J), defined by:

$$E(t) = \int_0^t I(t)dt \quad (1)$$

The pulse energy $E_o$ of the laser pulse is defined by $E_o=E(t=t_p)$ where the intensity pulse duration ($t_p$) represents the time during which 95% of the total energy of the laser pulse is delivered to the tissue. Depending on the application, other percentage values of the total energy may be used.

The energy delivery time $t_{ed}$ of the laser pulse is then defined as $t_{ed}=t_p-t_{eh}$, where the time $t_{eh}$ represents the time when the cumulative energy E(t) reaches half of the pulse energy, $E_o/2=E(t=t_{eh})$. Thus, the energy delivery $t_{ed}$ is the time span during which the second half of the pulse energy $E_o$ is delivered.

Figure 3:
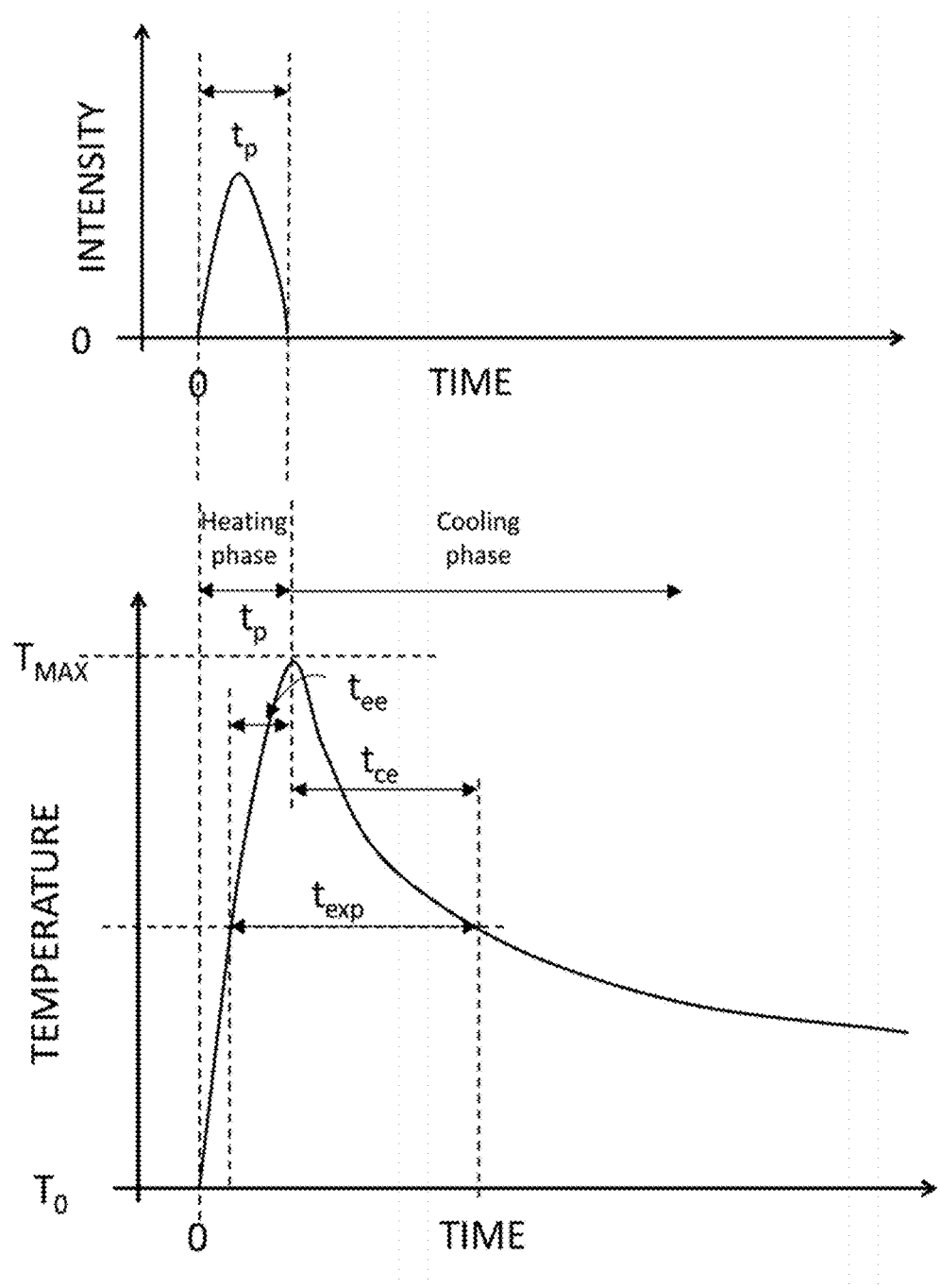

The upper part of FIG. 3 illustrates the intensity curve I(t) of a laser pulse, wherein, as mentioned above, the pulse duration $t_p$ is the time during which 95% of the total energy of the laser pulse is delivered to the tissue.

The lower part of FIG. 3 illustrates the corresponding temperature curve of the irradiated tissue surface. Starting with a temperature $T_o$ (the temperature of the tissue before the laser pulse impinges on the tissue surface), the laser pulse heats up the surface of the irradiated tissue to a maximal temperature $T_{max}$.

It is noted that the heating phase of the tissue lasts until time $t_p$, i.e., until the end of the energy delivery by the laser pulse. Then, the cooling phase begins during which the superficial layer of the tissue cools down in the absence of any external energy delivery to the tissue (see the lower part of FIG. 3). The cooling is predominantly caused by the fast diffusion of the heat from the thin superficial tissue layer to the underlying deeper tissue layers, and to a smaller extent also by a natural convection into the surrounding air or other surrounding media. It should be appreciated that diffusion-mediated cooling also takes place during the heating phase.

Defining the various quantities shown in FIG. 3 more precisely, we start with the thermal exposure time $t_{exp}$ which is the time span for which the treated tissue is exposed to elevated temperatures. Referring to the lower part of FIG. 3 which shows the temporally varying tissue surface temperature, we define the thermal exposure time $t_{exp}$ as the time difference $t_2-t_1$ between those two points on the temperature curve at which the temperature difference $\Delta T(t)=T(t)-T_o$ reaches half its maximum value, i.e., where $\Delta T(t_1)=\Delta T(t_2)=(T_{max}-T_o)/2$ holds. Thus, the thermal exposure time $t_{exp}$ corresponds to the FWHM (full width half maximum) value of the temperature curve. In other words, the thermal exposure time $t_{exp}$ is the time interval in which the temperature of the tissue surface is above $T_o+(T_{max}-T_o)/2$ Further, the energy exposure time $t_{ee}$ represents the heating phase contribution to the thermal exposure time $t_{exp}$, i.e. $t_{ee}=t_{peak}-t_i$ with $T(t_{peak})=T_{max}$ (cf. also the lower part of FIG. 3). Similarly, the cooling exposure time $t_{ce}$ represents the cooling phase contribution to the thermal exposure time $t_{exp}$ and can be defined as $t_{ce}=t_2-t_{peak}$. It should be noted that $t_{exp}=t_{ee}+t_{ce}$. As can be concluded from the temperature curve according to FIG. 3, the duration of the cooling phase has a considerable influence on the thermal exposure time $t_{exp}$.

Figure 4:
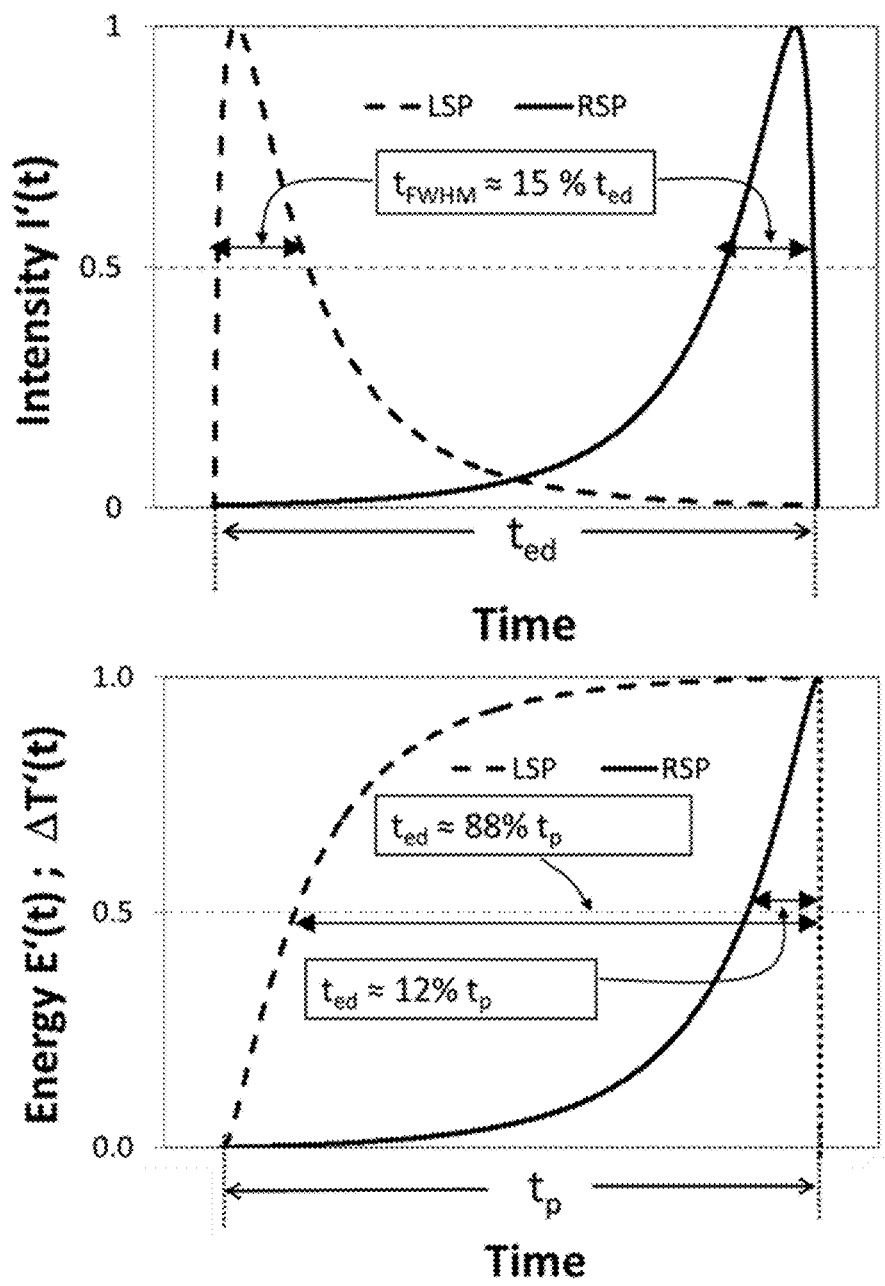

FIG. 4 illustrates the concept of the energy delivery time $t_{ed}$, wherein the upper part of FIG. 4 shows examples of a right shifted (RSP) and a left shifted (LSP) normalized laser intensity pulse with $I'(t)=I(t)/I_{max}$, wherein $I_{max}$ is the intensity's maximal value during a pulse. Both the RSP pulse and the LSP pulse have an FWHM pulse duration of $t_{FWHM}\approx 15\% \ t_p$.

The corresponding normalized cumulative energies $E'(t)=E(t)/E_o$ and normalized temporal evolutions of the temperature increase $\Delta T'(t)=T(t)/\Delta T_{max}$ are shown in the lower part of FIG. 4. As can be seen from the Figure, the energy delivery time is much larger for the LSP pulse ($t_{ed}\approx 88\% \ t_p$) than for the RSP pulse ($t_{ed}\approx 12\% \ t_p$). This is understandable, since the time when the first half of the pulse energy has been delivered to the tissue is much shorter for the LSP pulse than for the RSP pulse.

Finally, we would like to show that the energy delivery time $t_{ed}$ of the laser pulse is equal to the energy exposure time tee of the tissue:

During the laser pulse, the energy of the laser pulse rapidly flows into the superficial layer of the tissue within the penetration depth δ, and more slowly flows out of this layer deeper into the tissue by means of heat conduction (i.e., thermal diffusion). It is to be noted that in the absence of thermal diffusion, the temperature increase ΔT(t) at time t during the heating phase would be proportional with a proportionality coefficient k to the above-defined cumulative energy E(t) that has been delivered to the tissue until time t. Since the rate of heat conduction can be approximated to be also proportional to ΔT(t), the effect of heat diffusion is simply to reduce the proportionality coefficient to a smaller value (k'), with the resulting temperature increase ΔT(t) at time t during the heating phase being proportional to the above-defined cumulative energy E(t) that has been delivered to the tissue until time t. It is noted that both the energy delivery time $t_{ed}$ and the energy exposure time $t_{ee}$ start at the point where the cumulative energy curve E(t) and the temperature difference curve ΔT(t), respectively, reach its first half maximum. Further, both the energy delivery time $t_{ed}$ and the energy exposure time $t_{ee}$ end at time $t_p$ when the pulse energy of the laser pulse has been delivered. Thus, $t_{ed}=t_{ee}$ holds.

SUMMARY OF THE INVENTION

According to one aspect of the present invention, an apparatus for tissue regeneration is provided. The apparatus comprises means for generating at least one laser pulse comprising a wavelength; and means for directing the at least one laser pulse onto a tissue surface of a human or animal body, wherein the means for generating comprises control means to ensure that a sum of the pulse energies of the at least one laser pulse is selected so that the corresponding fluence on the tissue surface heats the tissue surface up to a maximal temperature $T_{max}$ between 70° C. and a tissue boiling temperature $T_b$. Further, the means for generating of the apparatus are adapted so that a delivery time $t_{ed}$ of the at least one laser pulse (during which the second half of the pulse energy is delivered) is sufficiently short so that, given the wavelength and thus a corresponding penetration depth δ of the at least one laser pulse, a thermal exposure time $t_{exp}$ of the tissue surface is shorter than 900 microseconds. Here, the thermal exposure time $t_{exp}$ of the tissue surface is defined as a time interval in which the temperature of the tissue surface is above $T_o+(T_{max}-T_o)/2$, wherein $T_o$ defines the initial temperature of the tissue surface, before the laser pulse arrives.

Contrary to the conventional wisdom, it has been discovered that the tissue can be heated up to a maximal temperature $T_{max}$ between 70° C. and $T_b$ without the occurrence of significant chemical damage to the tissue (in particular protein denaturalization), if the thermal exposure time of the tissue is sufficiently short, i.e., the tissue is heated up to high temperatures only during a short time span. In particular, it has been discovered that the thermal exposure time $t_{exp}$ of the tissue surface should be shorter than 900 microseconds, preferably smaller than 600 microseconds.

Preferably, the tissue is heated up to a maximal temperature $T_{max}$ between 90° C. and $T_b$ without the occurrence of significant chemical damage, more preferably to a maximal temperature $T_{max}$ between 120° C. and $T_b$.

It should be noted that the energy which is necessary to heat up the tissue to the above-specified temperature range can be distributed among more than one laser pulse. Further, the fluence (in Joule/cm$^2$) of the laser pulse on the tissue surface which is delivered by the at least one laser pulse is the relevant quantity for the achievable temperature. The fluence on the tissue surface depends on the pulse energy of laser pulse and also on how tightly this laser pulse is focused in the lateral direction(s). Similarly, the fluence on the tissue surface is also influenced by the distance between the apparatus which emits the laser pulse and the tissue surface.

It has been further discovered that the thermal exposure time of the tissue surface can be made shorter by making the energy delivery time $t_{ed}$ of the at least one laser pulse shorter. It should be noted that the time span $t_{ed}$ during which the second half of the pulse energy is delivered to the tissue is the relevant time span which must be kept short, in order to avoid tissue damage, since, during this time span, the tissue is already heated up by the first half of the pulse energy. Thus, during this time span $t_{ed}$, the tissue has an elevated temperature. This is also why the shape of the laser pulse plays an important role for the present invention.

Preferably, the energy delivery time $t_{ed}$ of the at least one laser pulse is smaller than 600 microseconds, more preferably smaller than 300 microseconds and most preferably smaller than 100 microseconds.

Another quantity which influences the thermal exposure time of the tissue surface is the penetration depth δ of the laser light within the tissue. In particular, the deeper the laser light penetrates into the tissue, the longer it takes for the tissue to cool down from the maximum temperature $T_{max}$.

It is noted that the wavelength of the laser determines how much light is absorbed by the tissue material. Thus, the wavelength of the laser determines the penetration depth δ.

Preferably, the means for generating of the apparatus are adapted to select the wavelength of the at least one laser pulse so that the penetration depth δ of the at least one laser pulse is smaller than 30 micrometers, preferably smaller than 10 micrometers, and most preferably shorter than 4 micrometers.

Preferably, the means for generating are adapted to select the wavelength of the at least one laser pulse between 2.6 and 3.2 micrometers or between 9.1 and 10.2 micrometers, in order to coincide with the mid-infrared water absorption peaks of water which is the major constituent of human and body tissues.

Quantitatively, it has been discovered that the thermal exposure time is given by the expression $t_{exp}=t_{ed}+(1/D)(δ+\sqrt{(2Dt_{ed})})^2$, wherein D=0.1 mm$^2$ s$^{-1}$ is the thermal diffusivity of the treated tissue.

According to another aspect of the present invention, the treated tissue has a critical temperature $T_{crit}$ which is the temperature up to which the tissue can be heated without the occurrence of significant damages (cf. further below for a more precise definition of $T_{crit}$). The critical temperature $T_{crit}$ depends on the thermal exposure time of the tissue and hence is determined by the parameters wavelength and energy delivery time of the delivered laser pulse.

If $T_{crit} \geq T_b$ the critical temperature $T_{crit}$ will not be reached even if the fluence F (in J/cm$^2$) of the laser pulse is chosen so large that the corresponding fluence on the tissue surface is greater than twice the ablation threshold of the tissue. The reason for not reaching the critical temperature $T_{crit}$ is that, at the boiling temperature $T_b$, micro-explosions of overheated tissue water occur which lead to the ejection of tissue material from the tissue surface. The ejection of tissue material is a cooling mechanism which prevents the further rise of the temperature even if the laser pulse delivers further energy to the tissue.

Preferably, the pulse energy ($E_o$) of the at least one laser pulse is chosen such that the corresponding fluence on the tissue surface is below the ablation threshold fluence, or not significantly above the ablation threshold fluence, i.e., the fluence on the tissue surface can be up to 4 times the ablation threshold fluence $F_{abl}$ of the tissue, more preferably up to 3 times the ablation threshold fluence and, most preferably, 1.5 times the ablation threshold fluence.

On the other hand, if $T_{crit}<T_b$, it is important that the maximum tissue temperature stays below the critical temperature $T_{crit}$ (for a given thermal exposure time of the tissue surface). Thus, the means for generating are adapted to select the pulse energy of the at least one laser pulse sufficiently small so that the tissue surface is heated to a maximal temperature $T_{max}$ which is smaller than the critical temperature $T_{crit}$ of the tissue.

According to another aspect of the present invention, the apparatus generates a plurality of laser pulses (i.e., a pulse train) which are directed to the tissue surface. In order to avoid an overheating of the tissue surface by the plurality of laser pulses, the means for generating are adapted to select the serial period ($t_{ser}$) between two successive laser pulses longer than about 10 $t_{exp}$, preferably longer than about 50 $t_{exp}$, and most preferably longer than about 150 $t_{exp}$.

On the other hand, in order that the deeper lying tissues do not cool down appreciably during the time span between two ESTART laser pulses, the serial period $t_{ser}$ should be shorter than about 3 seconds, preferably shorter than 1 second, most preferably shorter than 0.5 seconds.

Further, the number N of pulses of the pulse train should be selected so that the total duration of the pulse train $t_{DMR}=N \times t_{ser}$ is shorter than 30 seconds, preferably shorter than 10 seconds and, most preferably shorter than 5 seconds.

Further, instead of generating one spot S on the tissue surface by theat least one laser pulse, in certain preferred embodiments, the means for directing the at least one laser pulse are adapted so that the at least one laser pulse generates two or more spots on the tissue surface. Each of the at least one laser pulse may be adapted such as to generate two or more spots on the tissue surface.

Preferably, the means for directing the at least one laser pulse comprise a screen with holes which effects the generation of the two or more spots on the tissue surface. Alternatively, the means for directing comprise a lens array which effects the generation of the two or more spots. Further alternatively, the means for directing comprises a diffraction optics which uses interference effects for generating the two or more spots on the tissue surface. The inventors of the present application have realized that the approach of using a screen, which blocks a sizeable portion of the generated pulses, leads to heating problems when using relatively high fluence pulses. These can be ameliorated using the latter two approaches.

Preferably, the size d of each spot and the distance x between neighboring spots are selected so that the spots cover 25% to 65% of the treatment area.

Preferably, the size of the spots on the tissue surface is in the range of 0.3 mm≤d≤1.5 mm, more preferably in the range of 0.6 mm≤d≤1.2 mm.

According to a further aspect of the present invention, a method for tissue regeneration which uses a laser system is provided. The method comprises the following step: directing at least one laser pulse comprising a wavelength onto a tissue surface of a human or animal body, wherein the energy delivery time $t_{ed}$ of the at least one laser pulse, during which the second half of the pulse energy is delivered, is chosen sufficiently short, so that, given the wavelength and thus a corresponding penetration depth $\delta$ of the at least one laser pulse, a thermal exposure time $t_{exp}$ of the tissue surface is smaller than 900 microseconds. Besides, the sum of the pulse energies of the at least one laser pulse is selected so that the corresponding fluence heats the tissue surface up to a maximal temperature $T_{max}$ between 70° C. and a tissue boiling temperature $T_b$.

According to a further aspect of the present invention, an apparatus for treating male or female urinary symptoms or male erectile dysfunction is provided. Here, the term urinary symptoms refers to at least one of the following symptoms: incontinence (i.e., involuntary leakage), dysuria (i.e., painful urination), urgency and frequency of urination, or recurrent infections. The apparatus comprises means for generating at least one laser pulse comprising a wavelength; and means for introducing the at least one laser pulse into the urethra. The apparatus may comprise control means to ensure that a sum of the pulse energies of the at least one laser pulse is selected so that the corresponding fluence on the surface of the urethra heats the tissue surface up to a maximal temperature $T_{max}$ between 70° C. and a tissue boiling temperature $T_b$. Further, the means for generating of the apparatus may be adapted so that a delivery time $t_{ed}$ of the at least one laser pulse (during which the second half of the pulse energy is delivered) is sufficiently short so that, given the wavelength and thus a corresponding penetration depth $\delta$ of the at least one laser pulse, a thermal exposure time $t_{exp}$ of the surface of the urethra is shorter than 900 microseconds.

Here, it should be noted that the upper layer of the urethra is a mucosa layer which has a tissue boiling temperature $T_b$ which is approximately 250° C.

By introducing such laser pulses into the urethra, a mild hyperthermia is induced in the urethra and in the surrounding tissues.

When treating the male urethra, the afore-mentioned surrounding tissue consists of the periurethral erectile tissue (corpus spongiosum) which leads to the generation of new vessels, a regeneration of connective support and an improvement of the vascular function. As the vascular tissue and the fibro-connective support in all the tissue compartments is responsible for the maintenance of an erection, the laser therapy which uses the above-described apparatus helps in curing erectile dysfunction.

Similarly, when treating urinary symptoms it is known that the thickness of the urethral mucosa and the rich vascularization of the submucosa confer its sealing properties, since it is the main contributory factor of the reduction of both the caliber of the urethral opening and the radius of the urethral cylinder. The superficial warming process induced in the urethra improves the urethral trophism by promoting the vasodilation effect, and thus improves the performance of the intrinsic mechanism of continence by decreasing the radius of the urethra due to the improvement in the submucosal vascular plexus and the improvement in the thickness of the epithelium.

Preferably, the energy delivery time $t_{ed}$ of the at least one laser pulse is smaller than 600 microseconds, more preferably smaller than 300 microseconds and most preferably smaller than 100 microseconds.

Preferably, the means for generating of the apparatus are adapted to select the wavelength of the at least one laser pulse so that the penetration depth $\delta$ of the at least one laser pulse is smaller than 30 micrometers, preferably smaller than 10 micrometers, and most preferably shorter than 4 micrometers.

Preferably, the means for generating of the apparatus comprise two laser systems, wherein the two laser systems operate at different wavelengths.

The advantage of using two different wavelengths is that the two different wavelengths can achieve different clinical effects.

Preferably, the means for introducing the at least one laser pulse into the urethra comprises a cannula; and a handpiece which guides the at least one laser pulse to a treatment area on the surface of the urethra.

Preferably, the handpiece is fixedly connected to the cannula during the treatment of the urethra.

Preferably, the apparatus further comprises means for inspecting the urethra.

Preferably, the means for inspecting the urethra comprises a cannula; and an endoscope.

A further aspect of the present invention relates to the use of one or more laser pulses for treating urinary symptoms or erectile dysfunction.

According to a further aspect of the present invention, a method for treating urinary symptoms or erectile dysfunction is provided. The method comprises the following steps: introducing at least one laser pulse comprising a wavelength into the urethra; and guiding the at least one laser pulse to a treatment area on the surface of urethra, wherein the energy delivery time $t_{ed}$ of the at least one laser pulse, during which the second half of the pulse energy is delivered, is chosen sufficiently short, so that, given the wavelength and thus a corresponding penetration depth $\delta$ of the at least one laser pulse, a thermal exposure time $t_{exp}$ of the tissue surface is smaller than 900 microseconds. Besides, the sum of the pulse energies of the at least one laser pulse is selected so that the corresponding fluence heats the tissue surface up to a maximal temperature $T_{max}$ between 70° C. and a tissue boiling temperature $T_b$.

It is noted that the present invention encompasses all combinations of the above-described features, unless such a combination is not feasible (as it is, for example, self-contradictory or not working). In particular, the features described above with reference to an apparatus may be implemented as corresponding method steps. Also, the aspects and steps described in the present application may specifically be applied also for treating the urethra, even if not expressly mentioned.

The conventional approach for tissue regeneration focuses on a slow thermal pulsing of the connective tissue, in order to stimulate fibroblasts and other cells to respond to wound healing scenarios. In contrast, the approach according to the present invention is based on an indirect mechanism whereby the keratinocytes and other cells located in the superficial layer above the basement membrane are activated (i.e., triggered) by extremely fast and intense "heat shock" thermal pulses. The new collagen production is thus triggered not by the direct temperature elevation of the connective tissue but instead by the cross talk between the deeper lying fibroblasts and the superficially located keratinocytes that are activated by the fast thermal pulse triggering delivered by our innovative apparatus and method. In what follows the term ESTART (Epithelium Superficially Triggered Activation of Regeneration of Tissue) will be used from time to time to describe this new treatment apparatus and method.

The rapidly heated thin superficial tissue layer is then quickly cooled down by the fast diffusion of the generated heat to the underlying colder tissue layers. This is caused by the temperature gradient, which is very large in the superficial thin layer. As a result, the conductive cooling of the superficial layer is very effective, in contrast to within deeper connective tissue layers that remain moderately heated for a significantly longer time, owing to weaker heat flow from this region. Since the protein denaturation rate depends on temperature in a highly nonlinear manner, the short-lived high temperature gradient can be used to trigger deeper tissue regeneration without thermally damaging the epithelial tissue.

Therefore, as opposed to connective tissue heating where heat diffusion prolongs exposure times, it is the fast thermal diffusion from the heated thin superficial tissue layer that according to our innovation facilitates the generation of extremely short thermal exposure pulses.

The approach according to the present invention resembles the micro-needling technique that aims not to injure the keratinocytes but to stimulate them with superficial punctures and without any aggression to fibroblasts. Micro-needling has been introduced as a significantly less aggressive alternative to skin resurfacing or dermabrasion. Skin resurfacing and dermabrasion as used in aesthetic medicine for improving skin quality are based on "ablation" (destruction or wounding of superficial skin layers), which requires several weeks for healing that involves formation of new skin layers. Such procedures provoke an acute inflammatory response. A much less intense inflammatory response occurs following a microneedle perforation of the skin. The mechanism of action of micro-needling appears to be different from the mere inflammatory response to the localized "ablation", and seems to involve also induced cell proliferation by electrical signals. Since with micro-needling only a relatively small percentage of the skin is being affected, the treatment outcome is expected to be accordingly limited. On the other hand, the innovative ESTART concept according to our innovation can be viewed as a non-ablative thermal "needling" (i.e., triggering) of the total treated skin surface, with the action of the spatially sharp needles being replaced by the action of temporarily "sharp" but spatially broad thermal pulses.

The ESTART concept also resembles the laser induced thermal pre-conditioning. In this technique, the skin is pre-conditioned by being submitted to mild laser-induced heat shock prior to surgery. Laser-preconditioned incisions have been found to be two times stronger than control wounds that had not been laser pre-treated. However, the laser induced thermal pre-conditioning is performed over very long exposure times, on the order of minutes and therefore at temperatures below 50° C., and does not involve only epithelial tissues.

The ESTART concept may have applications in skin rejuvenation, gynecology, urology, dentistry and other medical areas. For example, in dentistry, ESTART may be used to promote wound healing in gingival tissue by increasing the number of fibroblasts. Additionally, regenerative effects on the alveolar bone are also expected.

DETAILED DESCRIPTION OF PREFERRED EMBODIMENTS

Figure 5:
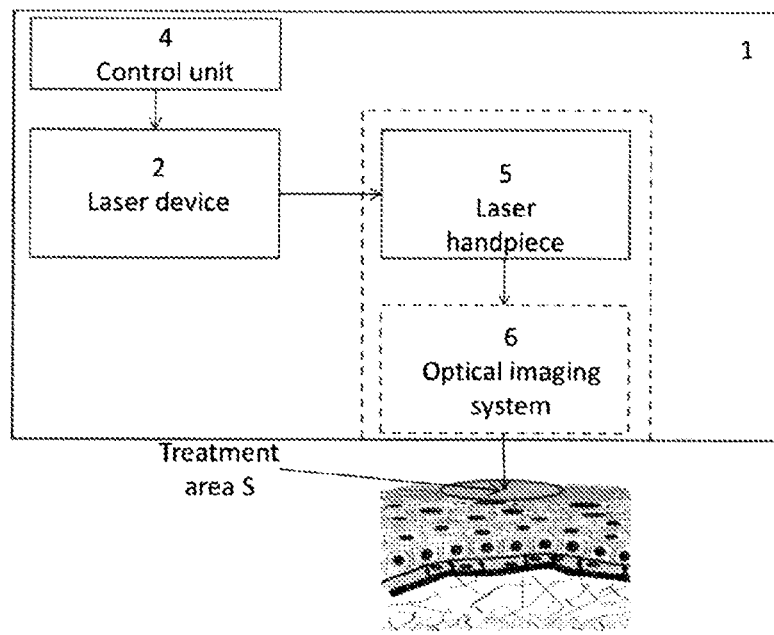
Figure 6:
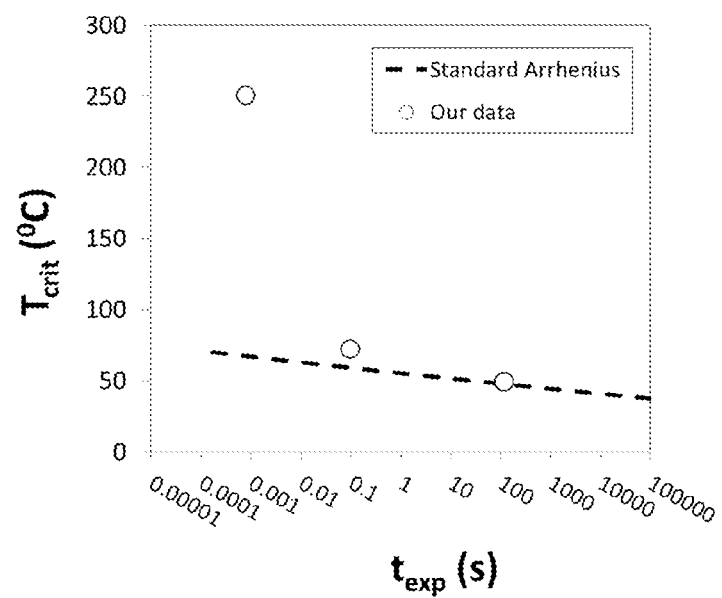
Figure 7:
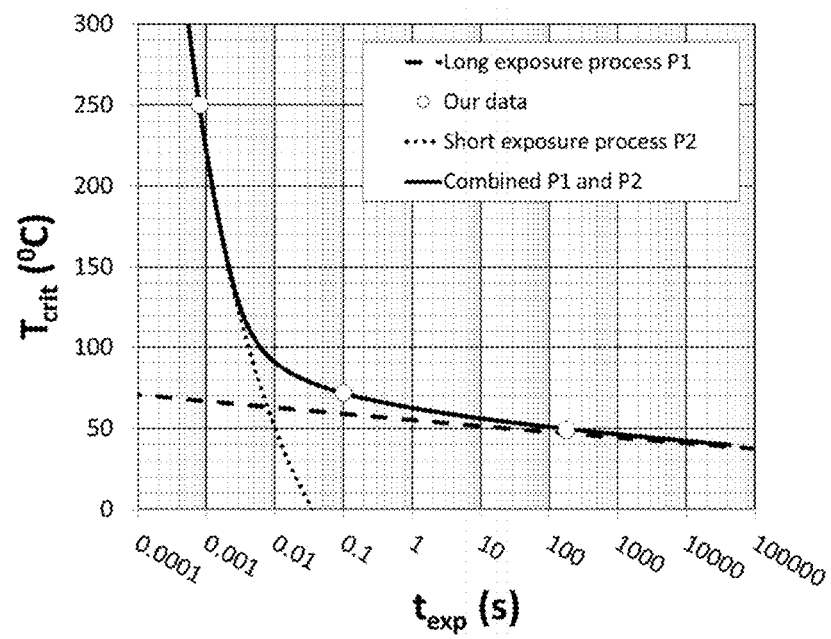
Figure 8:
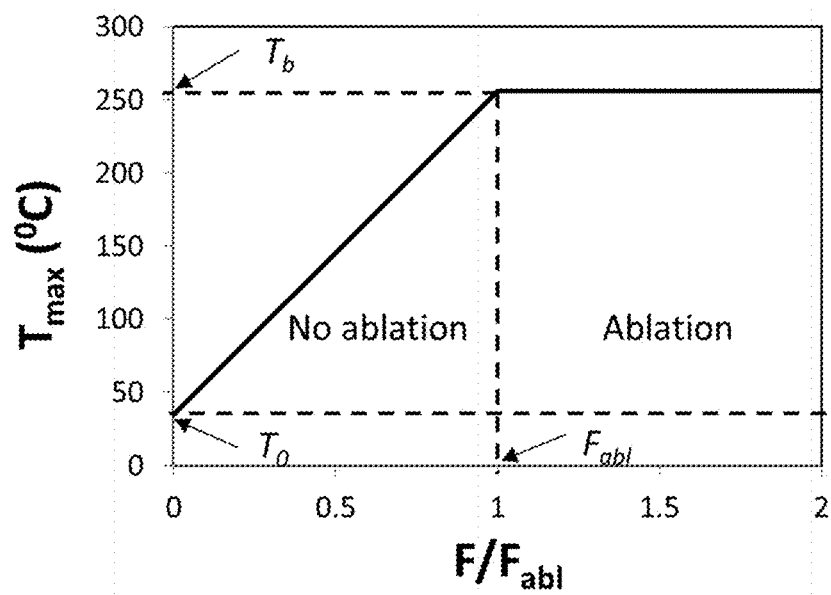
Figure 9:
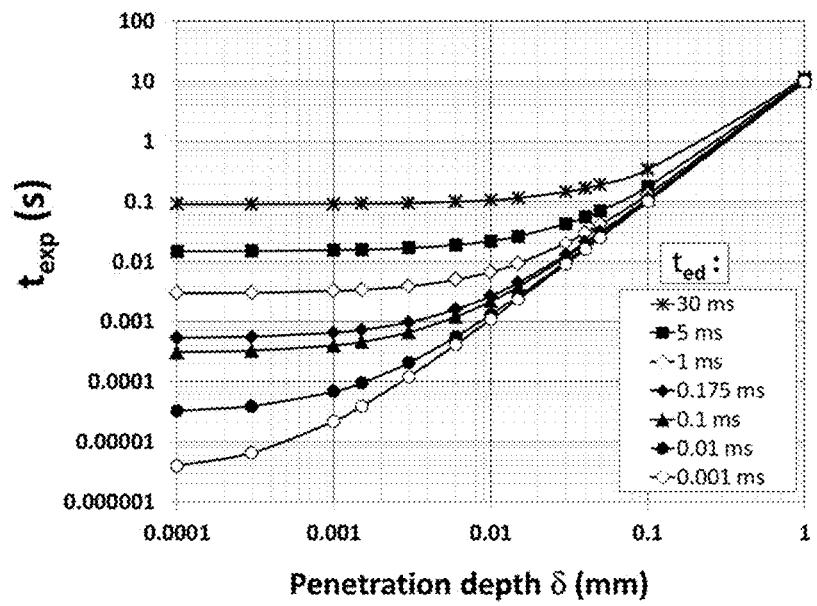
Figure 10:
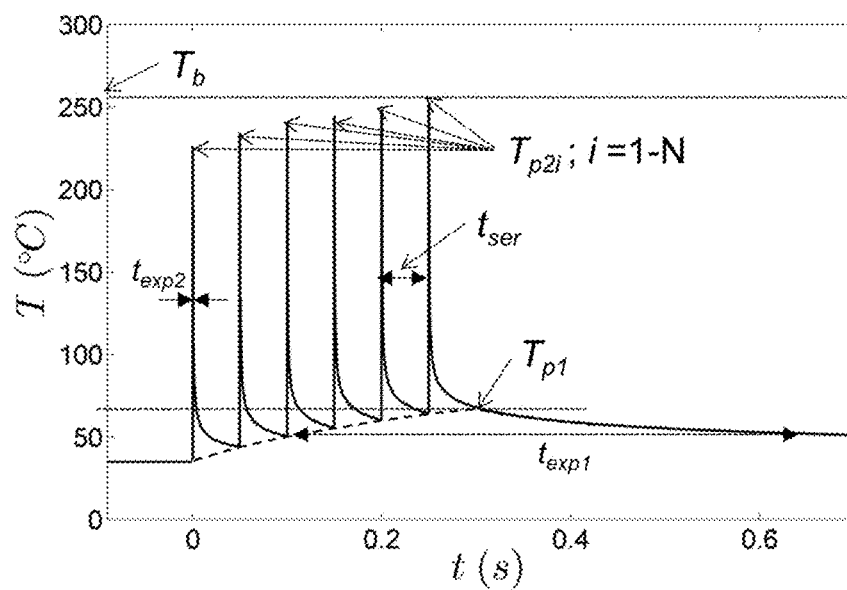
Figure 11:
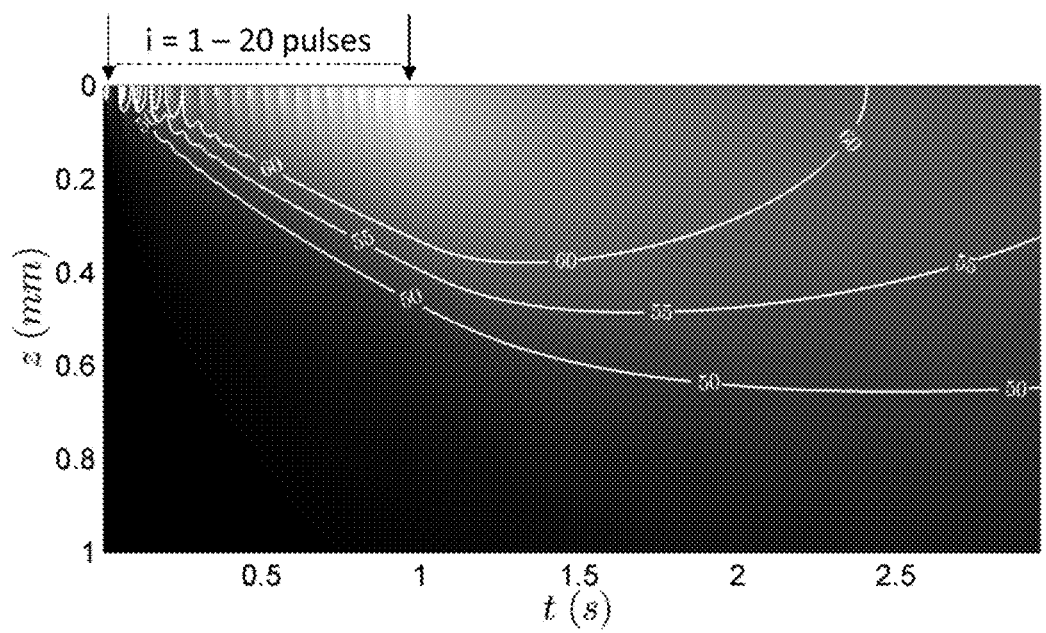
Figure 12:
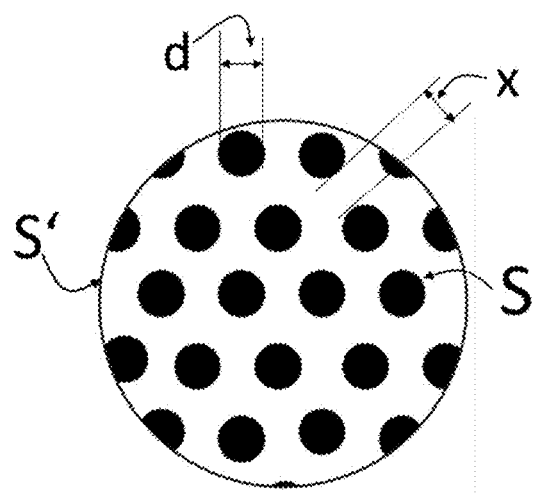
Figure 13:
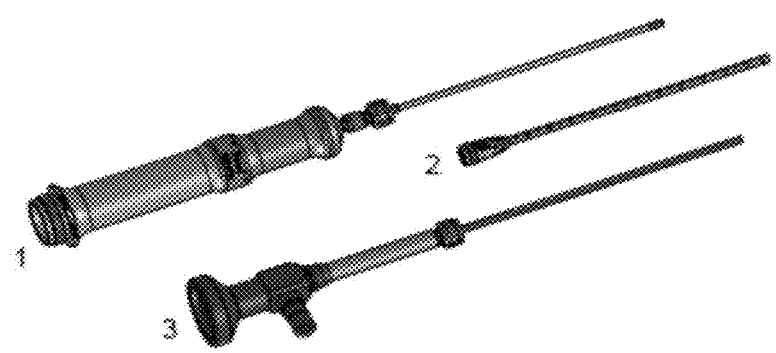

Some of the embodiments of the invention will be explained in the following with the aid of the Figures in more detail. It is shown in FIG. 1 a schematic illustration of the tissues surrounding the internal and external body surfaces;

FIG. 2 an illustration of the penetration depth δ within the irradiated tissue;

FIG. 3 the intensity of the delivered laser pulse (above) and the resulting thermal pulse on the tissue surface (below);

FIG. 4 the intensity of a of a "right shifted" and a "left shifted" laser pulse with the same FWHM energy pulse duration (above) and corresponding cumulative energy and thermal curves (below);

FIG. 5 an apparatus for tissue generation according to the present invention which comprises a laser system;

FIG. 6 the curve of critical temperature $T_{crit}$ over the thermal exposure time using standard Arrhenius parameters;

FIG. 7 the critical temperature over the thermal exposure times for human tissue which is based on clinical observations;

FIG. 8 the surface temperature $T_{max}$ at the end of a laser pulse as a function of the normalized fluence $F/F_{abl}$;

FIG. 9 the dependence of the thermal exposure time $t_{exp}$ on the energy penetration depth δ for different energy delivery times $t_{ed}$;

FIG. 10 the serial delivery of laser pulses with a goal to achieve dual mechanism regeneration;

FIG. 11 the temperature build-up during the serial delivery of laser pulses;

FIG. 12 the spatially patterned delivery of laser pulses;

FIG. 13 applicator elements for a laser treatment of the male or female urethra a) Exposure of the Tissue to a Laser Pulse An embodiment of the apparatus for tissue regeneration according to the present invention is the laser system 1 shown in FIG. 5. This laser system includes a laser device 2, a laser handpiece 5 and a control unit 4. The laser device generates a laser beam, while control unit is used for controlling and modifying the laser beam. Thus, the laser device and the control unit taken together are an embodiment of the means for generating according to the present invention.

Further, the laser handpiece 5 emits the laser beam so that it impinges on the tissue surface. Thus, the laser handpiece is an embodiment of the means for directing according to the present invention. Alternatively, an optical imaging system 6 (for example, a lens system) can be arranged between the laser handpiece and the tissue surface. Such an imaging system modifies the laser beam being emitted from the laser handpiece and then directs the modified beam to the tissue surface.

On the tissue surface, the extension of the laser beam is given by the spot S, wherein the spot S can be defined as the region of the tissue surface within which 90% of the total energy of the laser pulse is delivered to the tissue (i.e., the spot S corresponds to the smallest region on the tissue surface so that, during the delivery of the laser pulse, 90% of the total energy of the laser pulse is delivered to this region), cf. also FIG. 5. The spot S can also be referred as the treatment area. The laser system according to FIG. 2 operates in pulses, i.e. at least one laser pulse is emitted from the handpiece. Typically, the laser system generates a plurality of laser pulse, i.e. a train of laser pulses which are directed to the tissue surface.

As mentioned above, the laser pulse heats up the surface of the irradiated tissue to a maximal temperature $T_{max}$, wherein the heating phase lasts until the time when the pulse energy of the laser pulse has been delivered. Thereafter, the cooling phase of the tissue begins (cf. also the above definitions of the energy exposure time $t_{ee}$ and the cooling exposure time $t_{ce}$).

It is noted that the rate of the cooling can be enhanced by applying an external cooling to the epithelial surface before or immediately after the energy delivery. External cooling may be accomplished for example by using a cryogenic or liquid (for example, water) spray, a contact cooling or forced air.

b) Tissue Damage (Arrhenius Integral)

In the following, tissue damage means chemical damage of the tissue, in particular protein denaturalization which is an irreversible chemical reaction. It is noted that protein denaturalization is the most relevant process of all the chemical processes which lead to tissue damage.

Commonly, the metric for tissue damage (Ω) is the ratio of the concentration of native (undamaged) tissue before thermal exposure ($C_o$) to the concentration of native tissue at the end of the exposure time ($C_f$). The equation for the Arrhenius integral is $$\Omega = \ln(C_o/C_f) = A \int \exp(-E/RT) dt \quad (2)$$

where Ω is the tissue damage, A is the frequency factor (i.e. the damage rate in 1/sec), E is the activation energy (in J/mol), T is the temperature of exposure (in degrees K), R is the gas constant (R=8.32 J/mol K) and the integral is over the duration of the thermal pulse, Δt. Here, a square-shaped thermal pulse with a constant temperature during the duration of the thermal pulse is assumed.

The tissue damage kinetics can be characterized by a critical temperature ($T_{crit}$) which is defined as $$T_{crit} = E/(R \ln(A \Delta t)) \quad (3)$$

and represents the temperature at which the concentration of the undamaged tissue is reduced by a factor of e (i.e., Ω=1). While for long exposure times it is relatively easy to achieve approximately square-shaped thermal pulses, this becomes exceedingly difficult for exposure times shorter than approximately 1 second where the contribution of the slowly falling temperature during the cooling phase to the thermal exposure time becomes appreciable. Thus, for short exposure times, the shape of the temperature pulse more resembles a quasi "triangular" shape as represented in FIG. 3 above. For this reason and in order to be able to calculate critical temperatures for extremely short pulse durations, we redefine the Arrhenius parameters in such a manner that the critical temperature represents the maximal temperature during a FWHM thermal exposure time $t_{exp}$ for which Ω=1. Note that this does not affect the calculation of the critical temperature for longer pulse durations where nearly square shaped thermal pulses can be achieved, and therefore $t_{exp} \approx \Delta t$.

Published Arrhenius parameters vary but typical values (the "standard" values) for the Arrhenius parameters for skin which are obtained experimentally for exposure times $t_{exp} \geq 1$ sec are as follows: $A = 3.0 \cdot 10^{87}$ s$^{-1}$ and $E = 5.5 \cdot 10^8$ J/kmol. FIG. 6 shows the calculated expected dependence of the critical temperature on the exposure time, based on these standard parameters.

During standard regeneration treatments, the deeper lying layers of connective tissue are the tissue layers which one tries to thermally injure directly. Since deeper tissue layers remain heated for a long time (because of the weak flow of heat to the surrounding unheated tissues), this results in long cooling exposure times ($t_{ce}$), and consequently long overall exposure times ($t_{exp}$) of the connective tissue. Typical exposure times for the connective tissue are in the order of 10 seconds or longer. Consequently, as seen in FIG. 6, critical temperatures for the connective tissue are in the relatively low temperature range of 50 to 70° C. It is noted that, according to the standard Arrhenius parameters, the critical temperatures for the epithelium are similarly low.

During our clinical tests, however, we made the surprising discovery that, at extremely short exposure times, the viability of the skin cells is much higher than what would be expected from the observed cell viability for long thermal pulse durations (i.e., from the standard Arrhenius parameters). A dramatic change in the slope of the critical temperature versus thermal exposure time was observed (see our measured data on human skin represented by circles in FIG. 6). The exact reason for this change is not completely understood, but could be related to the cellular repair mechanism taking place at multi-second durations. The deviation from the Arrhenius law for shorter exposure times can not only be inferred from our limited clinical observations but also from the "Standard Guide for Heated System Surface Conditions that Produce Contact Burn Injuries", as published by The American Society for Testing and Materials (ASTM). This standard guide includes a chart which relates contact skin temperature to the time needed to cause a burn. The critical temperature curve is shown to start deviating from the standard Arrhenius law for thermal exposure times which are shorter than 10 sec. In particular, the critical temperatures for thermal exposure times $t_{exp} \leq 1$ sec are higher than what would be expected from the standard Arrhenius relationship.

Taking into account our clinically observed critical temperatures at short exposure times (represented by circles in FIGS. 6 and 7), we developed a prediction model for the critical temperatures over the complete range of exposure times (full line in FIG. 7). Our model is based on a discovery that the cell viability of any type of tissue can be described as a combined effect of two biochemical processes, $P_1$ and $P_2$, that dominate cell survival characteristics at very long (process $P_1$) and very short (process $P_2$) exposure times (See FIG. 7). Our analysis shows that the short exposure time process $P_2$ is characterized approximately by $A=8.0 \; 10^4$ $sec^{-1}$ and $E=1.8 \; 10^7$ J/kmol, while the long exposure time process ($P_2$) is characterized by the standard Arrhenius parameters as described above. It is to be expected that when attempting the regeneration of different types of tissues, critical temperatures will vary to a certain degree from tissue to tissue. However, since skin is known to be highly sensitive to temperature, it can be taken that FIG. 7 represents the worst case, and that for other types of epithelium and connective tissue, the critical temperatures will only be higher but not lower than what is shown in FIG. 7. Therefore, the safety considerations as described in this invention apply to all types of epithelium and connective tissues.

It is to be noted that ESTART treatments are based primarily on the characteristics of the short exposure time-biochemical process $P_2$. According to the curves shown in FIG. 7, no irreversible thermal injury is expected for temperatures up to and even above 250° C. provided that the thermal exposure time is shorter than approximately 1 msec.

c) Confined Water Boiling

In regeneration treatments, the goal is to locally heat up the tissue (in contrast to selective thermolysis treatments such as hair removal or vascular treatments where the goal is to selectively heat a specific spatially localized chromophore within the tissue). Since water is the major constituent of biological tissue, this means that the goal of regeneration treatments is to homogeneously heat up the tissue water. In the present method for tissue regeneration, the tissue water is heated up directly by absorbing the delivered laser light.

For example, if the epithelia is irradiated by radiation from an Er:YAG laser with wavelength $\lambda=2,940$ nm, the radiation is strongly absorbed within the superficial layer with a thickness of $\delta \approx 1$ µm. Gas $CO_2$ lasers emit at several wavelengths within the water absorption peak at 9 to 12 µm. The penetration depth in water of the $CO_2$ laser with wavelength $\lambda=10,640$ nm is approximately 20 times larger than for Er:YAG.

A microscopic numerical physical model was developed for the tissue water which is heated up directly within the penetration depth ($\delta$), wherein the penetration depth represents the inverse of the absorption coefficient within the tissue at the wavelength of the delivered laser pulse. Assuming that water is the major absorber, the tissue was treated as a homogenous material throughout epithelia and connective tissue. The thermodynamic behaviour of tissue water was combined with the elastic response of the surrounding solid tissue medium. This was complemented by a one-dimensional treatment of heat diffusion using a finite-difference scheme and by modelling protein denaturation kinetics with the Arrhenius integral.

It is to be appreciated that the tissue water plays an important role in our invention, since the heating of the tissue water to the confined boiling temperature ($T_b$) results in micro-explosions which eject over-heated tissue from the tissue surface. Thus, confined boiling of the tissue water leads to tissue ablation.

It should be further noted that this ablation mechanism which is based on confined boiling is different from other ablation mechanisms which involve strong acoustic transients, plasma formation, or transient bubble formation and which occur at higher laser intensities.

Further, it is noted that the ejection of over-heated tissue from the treated tissue acts as a cooling mechanism for the remaining tissue. As a consequence, even if further laser light is absorbed by the tissue water, the temperature of the treated tissue cannot increase beyond the temperature $T_b$ where confined boiling occurs, i.e., the maximal surface tissue temperature is effectively kept at $T_{max}=T_b$. FIG. 8 shows the maximal surface temperature $T_{max}$ of the tissue as a function of the normalized laser fluence $F/F_{abl}$.

Our measurements and calculations show that the ablation threshold fluence $F_{abl}$ can be calculated from the known penetration depth $\delta$ as:

$$F_{abl}=H_a \times \delta \qquad (4)$$

wherein $H_a$ is the specific heat of ablation for soft tissue with $H_a \approx 1.5 \times 10^4$ J/cm$^3$. As an example, $F_{abl}=1.5$ J/cm$^2$ for the Er:YAG laser.

The measured and calculated values of $T_b$ for human soft tissues vary to a certain degree (i.e., 248° C.$\leq T_b \leq$258° C.). Our calculations for a soft tissue give $T_b=256°$ C. For simplicity, we shall further assume in the following that $T_b \approx 250°$ C.

Therefore, as long as the thermal exposure time $t_{exp}$ is kept so short that the corresponding critical temperature $T_{crit}$ of the tissue is greater or equal to the confined boiling temperature ($T_{crit} \geq T_b$), the confined boiling of the tissue water will act as a regulating mechanism limiting which keeps the tissue temperature away from the critical temperature $T_{crit}$. As heating the tissue to the critical temperature $T_{crit}$ involves irreversible chemical tissue damage (protein denaturalization), the confined water boiling (CWB) mechanism represents a significant safety feature.

This safety mechanism is helpful in many practical circumstances. For example, when treating body cavities, the internal surface may not be regularly shaped and hence the delivered fluence, F (in J/cm²) and the generated heat may vary from one location to another. Besides, the energy source may not be always kept at the optimal distance or optimal angle with regard to the tissue surface, again resulting in a non-uniform heat pulse generation. And finally, a physician error can also occur. In all these cases, the CWB mechanism protects the patient from any irreversible injury and keeps the treatment within the safe ESTART limits.

It should be noted that the above-described ablation mechanism which is caused by the confined boiling of the tissue water is not harmful to the treated tissue. This is, since only a very thin layer of the tissue is removed by this ablation mechanism, providing that the fluence is not significantly above the ablation threshold. In particular, a typical ablation rate with an Er:YAG laser is 4 microns/(J/cm²). Therefore, even if the fluence exceeds the ablation threshold of about 1.5 J/cm² by a fluence factor $k_f=F_o/F_{abl}$ in the range of $k_f=1.25$ to 4, the maximal thickness of the removed layer does not exceed 3 to 18 microns. In the case that skin is treated, the removed layer is even smaller than the layer of dead cells on the surface of the skin which is constantly shredded away, in order to make room for newer cells to replace the old cells.

It should also be noted that our inventive regeneration apparatus and method are primarily intended to be non-ablative. However, in case the delivered fluence exceeds by accident or by intent or for any other reason the ablation threshold, the ablation by means of confined water boiling will not be harmful for the tissue, but will prevent harmful tissue damage due to protein denaturalization (if $T_{crit} \geq T_b$). This feature allows the practitioner to set the nominal fluence to a level where temperatures up to $T_b$ can be expected, without the risk of tissue damage in case the actual fluence during the treatment starts to deviate from the set nominal fluence.

d) Dependence of the Thermal Exposure Time $t_{exp}$ on the Penetration Depth $\delta$ and the Energy Delivery Time $t_{ed}$ In what follows, it will be assumed that the fluence F is homogeneous over the spot S. In case that the fluence is not homogeneous, the maximal fluence within the reduced spot S' over which the maximal fluence may be considered approximately homogeneous is the quantity to be considered. Also, it is the assumption that the dimensions of the spot S are such that the thermal diffusion in the lateral direction during the thermal exposure time can be ignored. Here, the lateral direction is to be understood as the direction along the tissue surface as opposed to the vertical direction that is directed into the tissue. When considering a circular spot S with a diameter d the thermal relaxation time (TRT) in the lateral direction can be calculated from the relation TRT=$d^2/16$ D where D=0.1 mm²/s is the thermal diffusivity of the soft tissue. As will be shown below, thermal exposure times shorter than about 5 ms are of particular interest for the present innovation. It can be therefore concluded that for spot diameters larger than about d=0.1 mm (TRT≈5 ms), the thermal diffusion in the lateral direction does not have a significant influence on $t_{exp}$. It should be appreciated that the spot S does not have to be circular. Therefore, the parameter d should be understood as the smallest dimension of the spot S in the lateral direction.

It is important to realize that the thermal exposure time ($t_{exp}$) is determined by the two quantities, penetration depth ($\delta$) and energy delivery time $t_{ed}$. This can be understood as follows: as shown above, $t_{exp}=t_{ed}+t_{ce}$ holds. Further, the cooling exposure time $t_{ce}$ is determined by the penetration depth $\delta$, since, as mentioned above, the cooling time depends on the thickness of the layer which has been heated up by the laser pulse. Our analysis shows that the cooling exposure time depends on $\delta$ and $t_{ed}$ as $$t_{ce} \approx \frac{1}{D}\left(\delta + \sqrt{2Dt_{ed}}\right)^2 \tag{5}$$

The physics behind this equation is as follows: the cooling time $t_{ce}$ of the superficial tissue layer after the heating phase can be calculated from $t_{ce}=(1/D) d_h^2$, where $d_h$ represents the diffusion length $d_h$ of the heated superficial tissue layer at the end of the heating phase and D≈0.1 mm² s⁻¹ is the thermal diffusivity of the tissue. The thickness $d_h$ is equal to the penetration depth $\delta$ plus an additional diffusion distance $d_d$ resulting from heat diffusion during the heating phase, i.e., $d_h=\delta+d_d$. It is known that the diffusion distance following a certain diffusion time $t_d$ is proportional to $\sqrt{(D t_d)}$, wherein the exact relation depends on the actual geometrical and temporal conditions. By fitting this expression to the numerical model, we determined that, for the conditions considered in the present invention, the diffusion distance is best described by $d_d \approx \sqrt{(2 D t_{ed})}$.

This dependence of the thermal exposure time $t_{exp}=t_{ed}+t_{ce}$ on the penetration depth $\delta$ and the energy delivery time $t_{ed}$ is illustrated in FIG. 9. As can be seen in FIG. 9 which is concerned with typical tissue regeneration lasers such as Er:YAG or CO₂ laser, the exposure time is $t_{exp}\approx0.7$ ms for the Er:YAG laser ($\lambda$=2,940 nm, $\delta\approx1$ μm) and $t_{exp}\approx4.6$ ms for the CO₂ laser ($\lambda$=10,640 nm, $\delta\approx15$ μm), wherein the energy delivery time of both lasers is $t_{ed}$=0.175 ms. Looking now at FIG. 7, the critical tissue temperature for the treatment with this particular Er:YAG device is $T_{crit}\approx260°$ C., while the critical tissue temperature for the treatment with this particular CO₂ laser device is much lower, namely $T_{crit}\approx105°$ C.

Since the critical temperature $T_{crit}$ of the treated tissue depends on the thermal exposure time $t_{exp}$ (cf. the above-discussed Arrhenius curves) and since the thermal exposure time $t_{exp}$ depends on the penetration depth $\delta$ and the energy delivery time $t_{ed}$, it follows that the critical temperature $T_{crit}$ of the treated tissue is also determined by the two parameters of the laser device, namely the penetration depth $\delta$ of the laser beam and the energy delivery time $t_{ed}$ of the laser pulse.

As shown in FIG. 7, the critical temperatures have the values of $T_{crit}$=120° C., 180° C. and 250° C. for the corresponding thermal exposure times $t_{exp}$=3.5 ms, 2 ms and 0.8 ms. Therefore, using FIG. 9, the maximal tissue surface temperatures $T_{max}$=120° C., 180° C. and 250° C. which can be safely imposed (i.e., $T_{max} \leq T_{crit}$) are subject to the condition that the corresponding optical penetration depth values of the treatment device are smaller or equal to about $\delta$=18 μm, 11 μm and 9 μm, wherein these values of $\delta$ are the maximal allowed optical penetration depths for the theoretical limit of infinitely short laser pulses. Similarly, using FIG. 9 again, for infinitely short penetration depths $\delta$, the maximal superficial temperatures above $T_{max}$=120° C., 180° C. or 250° C. can be safely imposed, if the energy delivery times $t_{ed}$ are shorter than correspondingly about $t_{ed}$=1.2 ms, 0.7 ms and 0.25 ms. With larger penetration depths, these limiting energy delivery times are correspondingly shortened.

e) Relevant Laser Parameters

As noted before, the penetration depth $\delta$ is the inverse of the absorption coefficient of the tissue at the wavelength $\lambda$ of the laser beam. Thus, for a given tissue to be treated, the wavelength of the laser beam determines the penetration depth $\delta$.

Therefore, by choosing appropriate laser parameters, namely an appropriate wavelength and an appropriate intensity pulse duration and shape, the thermal exposure time $t_{exp}$ (which, as seen above, is determined by the parameters δ and $t_{ed}$) and hence the corresponding critical temperature $T_{crit}$ for the treated tissue can be determined.

Using the relations shown in FIG. 9 for typical skin resurfacing lasers such as Er:YAG or $CO_2$, the thermal exposure time is $t_{exp} \approx 0.4$ ms for the Er:YAG laser (λ=2,940 nm, δ≈1 μm) and $t_{exp} \approx 3.9$ ms for the $CO_2$ laser (λ=10640 nm, δ15 μm). These numbers assume that the energy delivery times for both lasers of $t_{ed}$=0.1 ms. Taking into account FIG. 7, this translates into $T_{crit}$>300° C. for the Er:YAG laser and $T_{crit}$=110° C. for the $CO_2$ laser. Similarly, the Er,Cr:YSGG laser (λ=2,780 nm, δ=3 μm) with $t_{ed}$=0.1 ms, has an exposure time of $t_{exp} \approx 0.7$ ms which translates into $T_{crit} \approx 250$° C. It follows that, for this energy delivery time, only the Erbium lasers have a critical temperature above or at the boiling temperature $T_b$=250° C.

Laser parameters which lead to a critical temperature above the boiling temperature ($T_{crit} \geq T_b$) are particularly attractive for being used by the present apparatus and method for tissue regeneration, since, in this case, the tissue regeneration treatment can be safely operated without a special control of the fluence (F) of the laser pulse. This is, since the above-discussed confined water boiling (CWB) ensures that the critical temperature is not reached. Thus, the fluence of the used laser pulse can be several times above the ablation threshold.

Our analysis (see Table 1) shows that such a safe operation regime for tissue regeneration ($T_{crit} \geq T_b$) can be achieved with laser parameters which lead to a penetration depth of less than or equal to 6 μm provided that the energy delivery time is less than or equal to 50 μs. Similarly, for penetration depths less than or equal to 4 μm, the energy exposure time should be less than or equal to 100 μs, preferably less than or equal to 80 μs. For penetration depths less than or equal to 1 μm, the energy delivery time should be less than or equal to 250 μs, preferably less than or equal to 200 μs.

In order to achieve an extremely short penetration depth, the laser should have a wavelength which is close to the peak absorption for water at λ≈3,000 nm. Examples of such devices are the Er:YAG laser with λ=2,940 nm (with a corresponding penetration depth in water of 1 μm), or the Er,Cr:YSGG laser with λ=2,780 nm (penetration depth in water of δ≈3 μm). This leads to the requirement that the energy delivery time from the Er:YAG laser is chosen sufficiently short that the energy delivery time is shorter than or equal than about 250 μs, preferably less than or equal to about 200 μs. For the Er,Cr:YSGG laser, the energy delivery time of the laser pulse should be chosen sufficiently short that the energy delivery time is shorter than or equal to about 150 μs, preferably less than or equal to about 100 μs.

Laser pulses which lead to a critical temperature below the boiling temperature ($T_{crit} \leq T_b$) can also be used by the present apparatus and method for tissue regeneration provided that the fluence (F) of the energy pulse within the spot S is controlled such that the maximal temperature $T_{max}$ does not exceed the critical temperature of the tissue. In contrast, such a control of the fluence is not required if $T_{crit} \geq T_b$, as the CWB mechanism ensures that $T_{max}$ remains below or at $T_{crit}$.

For $T_{crit} \leq 180$° C. and for a penetration depth less than or equal to 10 μm, the energy exposure time should be less than or equal to 100 μs, preferably less than or equal to 50 μs. Similarly, for the device with the penetration depth less than or equal to 4 μm the energy delivery time should be less than or equal to 350 μs, preferably less than or equal to 300 μs. And for the penetration depth less than or equal to 1 μm the energy delivery time should be less than or equal to 600 μs, preferably less than or equal to 500 μs.

For $T_{crit} \leq 120$° C., and with the penetration depth less than or equal to 15 μm, the energy delivery time should be less than or equal to 100 μs, preferably less than or equal to 50 μs. Similarly, with the penetration depth less than or equal to 10 μm, the energy delivery time should be less than or equal to 350 μs, preferably less than or equal to 300 μs. And, for the penetration depth less than or equal to 4 μm the energy delivery time should be less than or equal to 800 μs, preferably less than or equal to 700 μs.

For $T_{crit} \leq 80$° C., and with the penetration depth less than or equal to 30 μm, the energy delivery time should be less than or equal to 1 ms, preferably less than or equal to 0.8 ms. Similarly, with the penetration depth less than or equal to 15 μm, the energy delivery time should be less than or equal to 3.5 ms, preferably less than or equal to 3 ms. And, for the penetration depth less than or equal to 4 μm the energy delivery time should be less than or equal to 6 ms, preferably less than or equal to 5.5 ms.

TABLE 1

| $T_{crit}$ | δ | $t_{ed}$ |
|---|---|---|
| 250° C. | ≤6 μm | ≤50 μs |
| | ≤4 μm | ≤80-100 μs |
| | ≤1 μm | ≤200-250 μs |
| 180° C. | ≤10 μm | ≤50-100 μs |
| | ≤4 μm | ≤300-350 μs |
| | ≤1 μm | ≤500-600 μs |
| 120° C. | ≤15 μm | ≤50-100 μs |
| | ≤10 μm | ≤300-350 μs |
| | ≤4 μm | ≤700-800 μs |
| 80° C. | ≤30 μm | ≤0.8-1 ms |
| | ≤15 μm | ≤3-3.5 ms |
| | ≤4 μm | ≤5.5-6 ms |

The single pulse fluences F required to elevate the surface temperature up to the maximal temperature $T_{max}$ can be calculated using FIG. 8 and Eq. 4 as $$F(T_{max}) = H_a \delta (T_{max} - T_o)/(T_b - T_o); T_{max} \leq T_b \qquad (6)$$

Assuming an Er:YAG laser (δ≈1 μm) and an initial tissue temperature of $T_0 = 35$° C., and taking into account the slight dependence of the threshold fluence on energy delivery time (threshold is higher for longer $t_{ed}$), the required fluences for exemplary $T_{max}$ are as shown in Table 2.

TABLE 2

| $T_{max}$ (° C.) | F (J/cm$^2$) |
|---|---|
| 80 | 0.2-0.4 |
| 120 | 0.5-0.7 |
| 180 | 0.9-1.1 |
| 256 | 1.4-1.6 |

It should be noted that our innovation is based on a linear interaction of the delivered laser pulse with the tissue. Therefore, when considering the reduction of the energy delivery time $t_{ed}$ (i.e., the duration of energy delivery) to the nanosecond or even shorter range, care must be taken that the delivered peak power of the laser pulse does not exceed the threshold for the non-linear interaction, since, in this case, the tissue would get damaged due to the tissue ionization at very high temperatures. Therefore, the energy delivery time $t_{ed}$ should not be shorter than approximately 100 ns.

f) Dual Mechanism Regeneration (DMR) Treatment

It is noted that a laser pulse is considered an ESTART laser pulse when its optical penetration depth δ and energy delivery time $t_{ed}$ are such that the critical temperature ($T_{crit}$) of the treated tissue (as defined by FIG. 7, and the corresponding Arrhenius parameters) is above 70° C., preferably above 120° C., even more preferably above 180° C., and most preferably above 250° C. Further, an ESTART* pulse is an ESTART pulse, characterized by $T_{crit} \geq 250°$ C.

A particular embodiment of our invention is the dual mechanism regeneration (DMR) apparatus which combines the fast (ESTART) superficial triggering of the epithelial surface primarily involving the short exposure process $P_2$ with the conventional temperature elevation of the deeper lying tissues primarily involving the long exposure process $P_1$. This is accomplished by generating and delivering a finite series of N ESTART laser pulses to the epithelial tissue, wherein the individual laser pulses are temporally separated from each other with a serial period $t_{ser}$ which is longer than the time required for the tissue surface to appreciably cool down after the preceding ESTART laser pulse, and shorter than 5 s, preferably shorter than 2 s, and most preferably shorter than 0.5 s, in order for the deeper lying (bulk) tissue not to cool down appreciably in-between ESTART pulses. In such a case the tissue temperature slowly builds up during the serial delivery of ESTART pulses, and the long exposure process $P_1$ takes place. In what follows we shall denote such a serial delivery of ESTART laser pulses, which results in a combined short exposure/long exposure treatment as a DMR pulse delivery and treatment.

FIG. 10 shows a typical temporal evolution of the tissue surface temperature T during a repetitive ESTART irradiation which, as an example, uses N=6 ESTART laser pulses with a serial period of $t_{ser}$=50 ms.

We characterize this DMR temporal evolution by two types of peak temperatures: i) "fast" temperature peaks $T_{p2i}$, belonging to individual ESTART laser pulses i (with i=1 to N) within the sequence of N pulses; and ii) a "slow" temperature peak $T_{p1}$ which describes the raise of the "base-line" temperature of the tissue surface from the first to the last ESTART pulse, before the temperature of the tissue surface decays again in the absence of further energy delivery. It is noted all the temperatures which are shown in FIG. 10 are measured at the centre of the spot S.

Roughly speaking, the tissue temperature $T_{p1}$ and the corresponding exposure time $t_{exp1}$ can be considered to be determined primarily by the long exposure process $P_1$, while the tissue temperature $T_{p2i}$ and corresponding $t_{exp1}$ is determined primarily by the characteristics of the short exposure process $P_2$. As described earlier, using a laser conforming to the ESTART conditions, the amount of cell injury that is incurred during fast temperature pulsing is limited, due to the very high critical temperatures under such short thermal exposure time ($t_{exp2}$) conditions. On the other hand, the tissue injury caused by the thermal base-line "pulse" (which lasts for seconds) can be considerable already for temperatures $T_{p1}$ above 55-65° C., as can be seen from FIG. 7. Therefore, controlling the slowly varying temperature elevations at the surface (and deeper within the tissue) during the DMR delivery is of critical importance for assuring the safety of the procedure.

The specific heat capacity of water which is the major constituent of tissues is $C_h$=4.2 J/cm³ K. The cumulative fluence $F_c = N \times F_o$ that is required to heat up the tissue volume extending to a depth $z_h$ of the tissue for an average temperature increase of $\Delta T_h$ can thus be estimated as $F_c \approx z_h C_h \Delta T_h$. Taking $\Delta T_h \approx 30°$ C., we obtain $F_c \approx 2.5$ J/cm² for $z_h \approx 0.2$ mm, $F_c \approx 13$ J/cm² for $z_h$=1 mm, and $F_c \approx 130$ J/cm² for $z_h$=10 mm. Therefore, the depth $z_h$ of the thermally treated tissues according to the slow exposure process $P_1$ is determined by the cumulatively delivered fluence $F_c = N \times F_o$ over the same spot S during a DMR pulse train (as set on the laser system's control box). In order not to "overheat" the deeper lying tissues, the cumulative fluence should not exceed $F_c \approx 150$ J/cm², preferably should be lower than 50 J/cm², and most preferably should be lower than 15 J/cm².

Similarly, the maximal surface temperature $T_{p1}$ is determined by setting the serial period $t_{ser}$ and the number N of the delivered ESTART pulses at control box. Our measurements and calculations show that, for a laser spot dimension of d>1.5 mm, the time span during which the maximal temperature difference $\Delta T_{p21} = T_{p21} - T_o$ of the first ESTART pulse drops down to $\Delta T_{f1} = k \Delta T_{p21}$, with k=0.01, k=0.02 and k=0.03 depends on $t_{exp}$ as $t_{1\%} \approx 150\ t_{exp}$, $t_{2\%} \approx 50\ t_{exp}$, and $t_{3\%} \approx 10\ t_{exp}$, correspondingly. The goal of the DMR serial delivery of pulses is that the epithelium does not get overheated while the heat is being "pumped" into the deeper lying tissues. Therefore, the serial period ($t_{ser}$) should be longer than about 10 $t_{exp}$, preferably longer than about 50 $t_{exp}$, and most preferably longer than about 150 $t_{exp}$. On the other hand, in order that the deeper lying tissues do not cool down appreciably during the time span between two ESTART laser pulses, the serial period $t_{ser}$ should be shorter than about 3 s, preferably shorter than 1 s, most preferably shorter than 0.5 s. Further, the total duration of the DMR pulse train $t_{DMR} = N \times t_{ser}$ should be shorter than 30 s, preferably shorter than 10 s, most preferably shorter than 5 s.

An example of the heat being pumped deeper into the tissue during a consecutive delivery of ESTART pulses is shown in FIG. 11 for the case of N=20 laser pulses, wherein δ=3 μm, $F_o$=0.8 J/cm² and $t_{ser}$=50 ms. The white lines represent isothermal curves with marked temperatures in ° C.

Considering that the maximal temperature increase during each ESTART laser pulse cannot be higher than $T_b$, this determines the lower limit for the required number of pulses as $N_{min} = F_e / F_{abl}$.

According to the present invention, one of the preferred embodiments is the delivery of ESTART* pulses, i.e., pulses satisfying $T_{crit} \geq T_b$. In this embodiment, ultimate safety can be achieved in a simple manner by controlling the number N of delivered ESTART* pulses, without the need for a precise control of the individual laser fluence $F_o$ which, as has been shown earlier, can vary uncontrollably during a treatment. Considering that the maximal temperature increase during each ESTART* laser pulse cannot be higher than $T_b$, this defines the maximal final temperature $T_{p1}$ (see FIG. 10) as $T_{p1} = T_o + N \times \Delta T_s$ where $\Delta T_s = k(T_b - T_o)$. Since $\Delta T_s$ is determined by the laser parameters $t_{ser}$ and $t_{exp}$ (further determined by δ and $t_{ed}$), which can be set by means of the control box, the desired maximal surface temperature $T_{p1}$ can be set by selecting $N \leq (T_{p1} - T_o)/(k(T_b - T_o))$ at the control box. This maximal surface temperature $T_{p1}$ holds under any fluence condition. For example, for $t_{ser}$=150 $t_{exp}$ (and therefore k=0.01), we determine that, by setting $N \leq 13$, $T_{p1}$ will never exceed 65° C. (regardless of $F_o$).

It should be appreciated that, for laser spot dimensions $d \leq 1.5$ mm, the thermal diffusion in the lateral direction(s) during the time span $t_{ser}$ can be appreciable, which contributes to the rate of temperature decay during the time span between two laser pulses. Therefore, for d i mm, the times $t_{2\%}$, $t_{2\%}$ or $t_{3\%}$ will be shorter than previously described, namely $t'_{1\%} < 75\ t_{exp}$, $t'_{2\%} < 35\ t_{exp}$, and $t'_{3\%} < 8\ t_{exp}$, correspondingly. Thus, using a small spot size allows the delivery of higher fluences at shorter serial times $t_{ser}$. For this reason, according to one of the preferred embodiments of present invention, the energy is delivered to the tissue in a "patterned" shape, wherein the laser beam irradiates a number (M) of individual spots S within the treatment area S' Each spot S having the size (e.g., diameter) d is separated from a neighbouring spot by the distance x (see FIG. 12). The spot size d and the distance x are chosen such that the spot size d is in the range of 0.3 mm≤d≤1.5 mm, and that the tissue coverage TC=(M×area(S))/area(S') (in %) is in the range of 25%≤TC≤65%. Further, the size (e.g., diameter) of the treatment area S' which comprise all the spots is in the range of 3 to 15 mm. These parameters ensure that, during the time span between two ESTART pulses (i.e., during $t_{ser}$), the thermal diffusion in the lateral direction spreads the heat which is generated by the laser radiation away from a localized spot S towards the surroundings of the spot, thus effectively spatially homogenizing the slowly varying temperature $T_{p1}$ across the area S'. Thus, intense heat shocks with short exposure time can be delivered to the localized spots S, without causing long-term overheating of the treatment area S'. This way, it is possible to create an intense heat "needling" on about 50% of the surface of the tissue, whereas the thermal injury in deeper layers is approximately homogeneous (in the lateral direction), since, in the deeper layers, the thermal diffusion spreads the heat in all directions.

There are several possibilities how a plurality of spots within the treatment area can be generated. First, one can use a screen with various holes in front of the laser handpiece. However, if the fluence of laser radiation becomes too large, the screen which blocks the laser radiation can become too hot. Alternatively, an array of lenses can be used for creating a pattern of distinct spots within the treatment area, wherein the laser beam illuminates the array of lenses. It should be noted that the array of lenses can comprise one layer of lenses which are transversally arranged with respect to the optical axis or, the array of lenses can comprise more than one layer of lenses which follow each other on the optical axis. Finally, diffraction optics can be used, in order to generate the pattern of distinct spots within the treatment area by using interference effects.

g) Treatment of the Male or Female Urethra by ESTART Pulses

Another aspect of the present invention concerns the treatment of male or female urinary symptoms and male erectile dysfunction by irradiating the urethra with ESTART laser pulses, i.e. laser pulses which have the above-described advantageous properties. The term erectile dysfunction, as used herein, refers to the inability or impaired ability of a male patient to experience penile erection. Apart from this, other conditions arising from degenerative changes of penile connective and vascular network can be treated by the method and the apparatus which is described below.

The term urinary symptoms as used herein refers to at least one of the following symptoms: incontinence (i.e., involuntary leakage), dysuria (i.e., painful urination), urgency and frequency of urination, and recurrent infections.

g1) Background Information

Erectile dysfunction, i.e., impairment of the ability to achieve or maintain an erection, is a fairly common medical condition which affects up to 40% men above the age of 60 and has a detrimental impact on quality of life.

Reasons for erectile dysfunction (ED) are different: they can be of psychological, hormonal, neurological or vascular origin. In older men, the main causes of ED are different impairments of vascular function, while, in younger men, other causes are more prevalent. The present invention concentrates on the vascular origin of erectile dysfunction.

The body of the penis is composed of three erectile columns, namely two lateral masses which are named "corpora cavernosa" and one median mass which is named "corpus spongiosum". The corpus spongiosum contains the urethra in the middle (see FIG. 1). The erectile tissues are bound together by fascial layers. The erectile tissues consist of connected compartments or sinusoids (also called trabeculae) which are divided by thin fibrous membrane, consisting mainly of connective tissue and smooth muscle fibres.

The penile arterial system is important for supplying the erectile tissues with blood, while the superficial, the intermediate and the deep venous systems are responsible for the venous drainage of the penis. The erection of the penis is a neurovascular mechanism, as neurologic stimuli result in a smooth muscle cell relaxation in the cavernous tissue, thus permitting the influx of arterial blood. At the same time, the venous outflow of blood is blocked due to the compression of the venous network against the fibrous envelope of the penis. This mechanism ensures that the erection is maintained.

Erection can be impaired by the degeneration of any of the above-mentioned structures and tissues which are important for the maintenance of the erection. In the case of vascular malfunction where either arterial inflow of blood or venous outflow is affected, problems with achieving and/or maintaining erection can occur. An important factor in the erection mechanism is also the fibrous "skeleton" which comprises the erectile tissues and the intra-corporeal fibrous network as well as smooth muscle cells which enable the relaxation of sinusoids and the influx of arterial blood.

The therapies for treating erectile dysfunctionality include psychological, pharmacological or therapies using energy based medical devices (the "EBM" devices). EBM devices employ light (laser light or otherwise, as for example the intense pulse light), radiofrequency (RF) radiation, ultrasound or other types of nonchemical energy. In the following, therapies which use laser devices are considered. In order to be effective, the laser has to deliver enough energy and/or power to thermally affect the structure or the function of the tissues.

Apart from erectile dysfunction, the male or female urinary symptoms represent another debilitating condition. The reason is often age-related degeneration (atrophy) of the urethral mucosal seal, which leads to the unwanted leakage of urine and other symptoms.

The present invention involves a laser-based therapy for stimulation and regeneration of the urethral and surrounding tissues in order to treat male erectile dysfunction, urinary symptoms, and other conditions arising from degenerative changes of urethral and surrounding (including penile) connective and vascular network. In what follows the term "erectile dysfunction" will be used occasionally to represent all conditions arising from degenerative changes of urethral and surrounding (including penile) connective and vascular network. Similarly, the term "penile tissue" will be occasionally used to represent both male and female urethral and surrounding tissues.

Most of the previous therapies involve delivering a certain type of a non-chemical energy extra-corporeally to the penile tissue. One of the earlier EBM devices that have been proposed for the stimulation of the hemodynamic activity within the penis is the ultrasound device (WO9912514). The method involves coupling an ultrasound device to the outer surface of the penis and then transmitting the ultrasound energy into the penis.

Delivering laser radiation intra-urethrally to reverse degenerative changes of penile connective and vascular network has been avoided, primarily because of the concerns that the locally delivered laser energy will be transformed into heat which damages the urethra. During the transurethral microwave (i.e., radiofrequency) therapy of the prostate, the energy is delivered through the urethra but not to the urethra. According to this therapy, an instrument (called an antenna) which sends out microwave energy is inserted through the urethra to a location inside the prostate, wherein the microwave energy is used to heat up the inside of the prostate. In particular, it is the goal that that the temperature inside the prostate becomes high enough to kill some of the tissue. During the transurethral microwave therapy special cautions are taken to prevent that too much heat damages the wall of the urethra, namely by circulating a cooling fluid around the microwave antenna. In addition, to prevent the temperature from getting too high outside the prostate, a temperature sensor is inserted into the patient's rectum during the therapy. If the temperature in the rectum increases too much, the treatment is turned off until the temperature falls again.

g2) Delivering the ESTART Pulses Inside the Urethra

The above-mentioned discoveries have prompted the inventors of the present application to use laser thermotherapy to treat conditions that arise from degenerative changes in the urethral and surrounding tissues, such as the penile urethral and erectile tissues which lead to various health problems, the most serious being erectile dysfunction, male urinary incontinence, urethral stenosis, and other urinary symptoms.

In an embodiment of the present invention, an intra-urethral cannula is inserted into the urethral opening. Here, a handpiece guiding the laser beam is connected to the cannula. Alternatively, the cannula is inserted into the urethral opening first, and then the handpiece is inserted into the cannula. It should be noted that the handpiece receives the laser beam from a laser device which generates the laser beam.

The head of cannula is positioned at that region of the urethra which shall be treated. This way, the laser pulses are delivered to the region of the urethra which shall be treated. As the laser pulse is absorbed in the upper layer of the urethra (the epithelium), the laser energy is transferred into heat. The pulse energy is strictly controlled so that transient pulses of increased temperature are generated in the urethral epithelia. Further, the wavelength and the pulse shape of the laser pulse are selected so that the penetration depth inside the epithelium is sufficiently small and the energy delivery time of the laser pulse is sufficiently short (this means: the laser pulses are ESTART pulses). In particular, the penetration depth $\delta$ should be less than or equal to 10 μm provided that the energy delivery time of the laser pulse is less than or equal to 50 μs. Alternatively, for a penetration depth less than or equal to 4 μm, the energy delivery time should be less than or equal to 250 μs, preferably less than or equal to 150 μs. Finally, for a penetration depth less than or equal to 1 μm the energy exposure time should be less than or equal to 350 μs, preferably less than or equal to 200 μs.

It should be noted that the cannula together with the handpiece can be slowly pulled out of the urethra so that large sections of the urethra and even the entire urethra can be treated by means of laser pulses.

By using ESTART pulses with an appropriate wavelength and pulse shape, no or only minimal thermal damage is caused in the urethral epithelial surface, if the fluence (in $J/cm^2$) for the delivered energy to the urethral epithelial surface is appropriately chosen. A particular broad range of "safe" fluences is possible, if the critical temperature $T_{crit}$ of the tissue (for the corresponding thermal exposure time of the tissue surface) is higher than the tissue boiling temperature $T_b$. As described above, the temperature of the tissue cannot rise above the temperature $T_b$ in this case, so that no irreversible damage to the tissue occurs. In this context, it should be noted that the internal surface of the urethra is not regularly shaped. Also, the handpiece may not be always kept at the optimal distance or optimal angle with respect to the epithelial surface. This may result in a non-uniform delivery of the fluence, and consequently in a non-uniform generation of heat in the radial and longitudinal direction of the urethral cavity. And finally, a physician error can also occur. In all these cases, the confined boiling mechanism protects the patient from any irreversible damage and hence represents a significant safety feature.

Optionally, the section of urethra which needs to be penetrated during the laser treatment can be inspected before the laser treatment, i.e., before the cannula and the handpiece are inserted into the urethra. Here, it should be noted that, as mentioned, the male urethra is curved and significantly longer than the female urethra so that there is a danger to damage it during a laser treatment. Thus, it is advantageous to observe the urethral region which lies in front of the cannula when penetrating the urethra by means of a cannula. This is possible by introducing an endoscope into the cannula, wherein any endoscope which has a smaller external tube diameter than the opening of the cannula can be used. Thus, it is the cannula with the inserted endoscope that is first slowly inserted into the urethra, wherein the endoscope enables the operator to constantly monitor the introduction of the cannula into the urethra. Once the cannula is placed at the appropriate depth, the endoscope is removed, and the handpiece (more precisely, the end of the handpiece which guides the waveguide) is introduced into the cannula.

According to the present laser treatment of the urethra, thermal energy is deposited throughout the urethra by retrieving the cannula (together with the handpiece) outwards while at the same time emitting the laser pulses. The resulting intense thermal pulsing within the epithelial tissue leads to an intense signalling between the epithelia and the underlying connective tissues which causes the deeper lying tissues to initiate a regeneration process. Additionally, the superficial intense epithelial triggering may be combined with the conventional slower temperature build-up within the connective tissue (cf. the above-described dual mechanism regeneration (DMR) treatment). This is accomplished by delivering a series of short, sharp thermal pulses to the epithelial tissue, wherein the individual thermal pulses are temporarily separated by the serial period, $t_{ser}$, which is less than about 50 Hz, preferably less than about 16 Hz. In particular, the above-described dual mechanism regeneration (DMR) treatment which uses pulse trains can be also applied to the treatment of the urethra.

This way, a mild hyperthermia is induced in the urethra and the periurethral erectile tissue (corpus spongiosum) which leads to the of new vessels, a regeneration of connective support and an improvement of the vascular function. In one of the preferred embodiment of the invention, the method comprises an additional step which is external and can be performed simultaneously with intra-urethral laser treatment, namely delivering thermal energy to the anterior surface of the penis. This delivery of thermal energy leads heating pulses for the other two erectile tissue compartments, the two corpora cavernosa. Thus, the resulting effect of the therapy is the regeneration of the vascular tissue and the fibro-connective support in all tissue compartments which are together most responsible for the maintenance of an erection.

g3) Apparatus for Treating Urinary Symptoms and Erectile Dysfunction by Means of Laser Pules FIG. 13 illustrates applicator elements which can be used for performing the above-described treatment method of the urethra by means of laser pulses. The applicator elements comprise handpiece 1, cannula 2 and endoscope 3.

As described above, cannula 2 may be first inserted into the urethra, and then handpiece 1 is inserted into cannula 2. Similarly, for the inspection of the urethra, endoscope 3 is inserted into cannula 2. Thus, the handpiece and the endoscope are designed in a manner that they can be inserted into the cannula, wherein the final position of handpiece/endoscope is optionally locked (e.g., screwed) to the cannula. It should be noted that the two applicator elements cannula 2 and handpiece 1 are an embodiment of the means for introducing a laser pulse into the urethra according to the present invention. Further, the two applicator elements cannula 2 and endoscope 3 are an embodiment of the means for inspecting the urethra according to the present invention.

Turning to the handpiece 1 in more detail, the thicker part of handpiece 1 contains a focusing lens which focuses the laser beam into a hollow waveguide, which is included in the thinner part of the handpiece. At the end of the hollow waveguide, the laser beam then spreads out of the hollow waveguide at an angle of 5-30 degree, preferably 5-15 degree, particularly preferably ca. 11 degree. Since the inner side of the hollow waveguide (which is inserted into the cannula 2 when preforming the treatment) must not contact any liquid or small particles, cannula 2 is covered with a sapphire transparent protective window which protects the hollow waveguide of the handpiece 1.

Cannula 2 which is hollow should have an outer diameter so that the canal of the urethra is widened in a smooth manner. This way, the laser beam can evenly irradiate the first few millimeters of urethra wall which are located in front of the cannula. As mentioned, another function of the cannula is the protection of the hollow waveguide tip and the endoscope during the treatment. After the treatment, only the cannula needs to be cleaned and sterilized. Besides, cannula 2 comprises an engraved scale which enables the operator to move the cannula along the urethra in a controlled manner.

In an example, a laser device according to the invention may comprise at least one laser system for generating at least one laser beam, and at least one optical delivery system for the generated at least laser beam. Particularly, the laser device may comprise two integrated individual laser systems, each having an individual laser source. The laser device may further comprise a control unit, similarly as described with reference to FIG. 5, for controlling the operation of the at least one laser source of the at least one laser system, including generated laser beam parameters. The control unit may control the operation of both laser sources and is therefore integral part of both laser systems. However, each laser system may also have its own control unit. It should be noted that the described laser device may be an embodiment of the means for generating at least one laser pulse comprising a wavelength according to the present invention.

In a preferred embodiment, an optical delivery system includes an articulated arm and a manually guided laser treatment head or handpiece, as described further above, which is connected to the distal end of the articulated arm, wherein the laser light is transmitted, relayed, delivered, and/or guided from either one or both laser systems through the articulated arm and the laser treatment head to a target. Preferably, the articulated arm can be an Optoflex articulated arm available from Fotona, d.o.o. (Slovenia, EU). In a preferred embodiment, additionally or alternatively, an optical delivery system may be provided, wherein, instead of the articulated arm, a flexible elongated delivery fiber for guiding the laser beam from either one or both laser systems is incorporated. Either one of the optical delivery systems might be used in connection with either one of the two laser systems, thereby guiding either one or both of the laser beams provided by the two laser systems. A handpiece as described further above may also be attached to the distal end of the elongated fiber.

Alternatively, one or both laser sources may be built into the handpiece Moreover, the control unit, or the complete laser systems may be built into the handpiece as well.

According to the invention, the wavelength of the laser beam which is generated by the first laser system is in a range from 2.5 µm to 3.5 µm, preferably 2.7 µm to 3 µm. The wavelength of the laser beam generated by the second laser system is in the range from 0.8 µm to 11 µm, preferably 9 µm to 11 µm. Examples for suitable laser systems are an Er:YAG laser ($\lambda$=2.94 mm) or a $CO_2$ laser ($\lambda$=9 to 11 mm).

The invention claimed is:

1. An apparatus for non-ablative tissue regeneration comprising:
   a laser for generating laser pulses having a wavelength and a pulse energy;
   a control unit for controlling the laser; and
   a cannula for delivering the laser pulses onto a surface of a urethra of a human body; and
   wherein the control unit comprises control instructions configured to control the laser so that a delivery time $t_{ed}$ of the laser pulses, during which the second half of the laser pulse energy is delivered, is sufficiently short so that, given the wavelength and thus a corresponding urethra penetration depth d of the laser pulses, $t_{ed}+(1/D)(\delta+\sqrt{2Dt_{ed}})^2$ is shorter than 900 microseconds, wherein $D=0.1$ mm$^2$s$^{-1}$; and
   wherein the control instructions are configured to control the laser such that a sum of the pulse energies of the laser pulses heats the surface of the urethra to a maximal temperature $T_{max}$ between 70° C. and a urethra boiling temperature $T_b$.

2. The apparatus according to claim 1, wherein $t_{ed}+(1/D)(\delta+\sqrt{2Dt_{ed}})^2$ corresponds to a time interval in which the temperature of the surface of the urethra is above $T_0(T_{max}-T_0)/2$, wherein To defines an initial temperature of the surface of the urethra before the laser pulses are delivered onto the surface of the urethra, wherein $T_{max}$ defines a maximal temperature of the surface of the urethra resulting from the delivered laser pulses.

3. The apparatus according to claim 1, wherein the control instructions are configured to select the wavelength of the laser pulses so that the penetration depth $\delta$ of the laser pulses are smaller than 30 micrometers, preferably smaller than 10 micrometers.

4. The apparatus according to claim 3, wherein the control instructions are configured to select the wavelength of the laser pulses between 2.6 and 3.2 micrometers or between 9.1 and 10.2 micrometers.

5. The apparatus according to claim 1, wherein the control instructions are configured to control the laser so that the energy delivery time $t_{ed}$ of the laser pulses is shorter than 600 microseconds.

6. The apparatus according to claim 1, wherein, for $t_{ed}+(1/D)(\delta+\sqrt{2Dt_{ed}})^2$ being shorter than 900 microseconds, the treated urethra has a critical temperature $T_{crit}$ which is greater or equal to the urethra boiling temperature $T_b$; and
wherein the control instructions are configured to select the pulse energy of the laser pulses so large that the corresponding fluence on the surface of the urethra is up to 4 times the ablation threshold fluence $F_{abl}$ of the urethra.

7. The apparatus according to claim 1, wherein, for $t_{ed}+(1/D)(\delta+\sqrt{2Dt_{ed}})^2$ being shorter than 900 microseconds, the treated urethra has a critical temperature $T_{crit}$ which is smaller than the urethra boiling temperature $T_b$; and
wherein the control instructions are configured to select the pulse energy of the laser pulses sufficiently small so that the surface of the urethra is heated to a maximal temperature $T_{max}$ which is smaller than the critical temperature $T_{crit}$ of the urethra.

8. The apparatus according to claim 1, wherein the control instructions are configured to generate a plurality of laser pulses which are directed to the surface of the urethra; and
wherein the control instructions are configured to select the time $t_{ser}$ between two successive laser pulses longer than 10 times $t_{ed}+(1/D)(\delta+\sqrt{2Dt_{ed}})^2$, preferably longer than 40 times $t_{ed}+(1/D)(\delta+\sqrt{2Dt_{ed}})^2$.

9. The apparatus according to claim 8, wherein the control instructions are configured to select the time $t_{ser}$ between two successive laser pulses shorter than 3 seconds, preferably shorter than 1 second.

10. The apparatus according to claim 8, wherein the control instructions are configured to select the number of laser pulses so that the total duration of the pulse train is shorter than 30 seconds.

11. The apparatus according to claim 1, wherein the cannula is adapted so that the laser pulses generate two or more spots on the surface of the urethra, preferably with a spot size d in the range 0.3 mm≤d≤1.5 mm.

12. A method for non-ablative tissue regeneration which uses a laser system and comprises the following step;
directing, with a cannula, laser pulses comprising a wavelength and a pulse energy onto a surface of a urethra of a human body;
wherein the energy delivery time $t_{ed}$ of the laser pulses, during which the second half of the laser pulse energy is delivered, is chosen sufficiently short, so that, given the wavelength and thus a corresponding urethra penetration depth 5 of the laser pulses, $t_{ed}+(1/D)(\delta+\sqrt{2Dt_{ed}})^2$ is smaller than 900 microseconds, wherein $D=0.1$ mm$^2$s$^{-1}$; and
wherein the laser is controlled such that a sum of the pulse energies of the laser pulses heat the surface of the urethra to a maximal temperature $T_{max}$ between 70° C. and a urethra boiling temperature $T_b$.

\* \* \* \* \*